United States Patent [19]

Fukami et al.

[11] Patent Number: 4,976,773
[45] Date of Patent: Dec. 11, 1990

[54] HERBICIDALLY ACTIVE PHENOXYALKANECARBOXYLIC ACID DERIVATIVES

[75] Inventors: Harukazu Fukami, Kyoto; Naoki Higuchi, Ikeda; Naoko Kawaguchi, Moriguchi; Masaki Hashimoto, Ibaraki; Kinya Ide, Kusatsu; Toshio Takahashi, Nishinomiya, all of Japan

[73] Assignee: Suntory Limited, Osaka, Japan

[21] Appl. No.: 230,481

[22] Filed: Aug. 10, 1988

[30] Foreign Application Priority Data

Aug. 11, 1987 [JP] Japan ................ 62-199040
Aug. 11, 1987 [JP] Japan ................ 62-199041
Oct. 23, 1987 [JP] Japan ................ 62-266563
Jan. 4, 1988 [JP] Japan ................ 63-000010

[51] Int. Cl.$^5$ .................. C07D 213/64; A01N 43/40
[52] U.S. Cl. .......................... 71/94; 546/300; 546/302
[58] Field of Search ................ 546/300, 302; 71/94

[56] References Cited

U.S. PATENT DOCUMENTS 4,175,947 11/1989 Koch et al. ................ 71/88
4,425,157 1/1984 Rempfler et al. .......... 71/94
4,526,608 7/1985 Lee .............................. 71/94

Primary Examiner—Alan L. Rotman
Attorney, Agent, or Firm—Burns, Doane, Swecker & Mathis

[57] ABSTRACT

A compound of the formula:

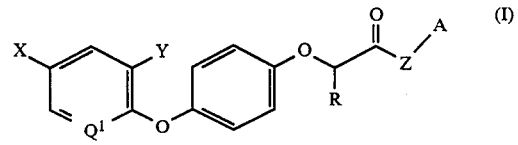

wherein $Q^1$ is CH or N; R is H or $C_1$-$C_5$ alkyl; X is H, halogen, $CF_3$, or $NO_2$; Y is H or halogen; Z is —O— or —NH—; A is

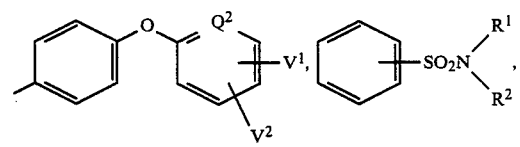

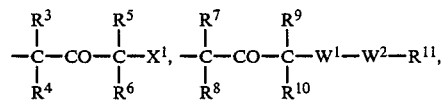

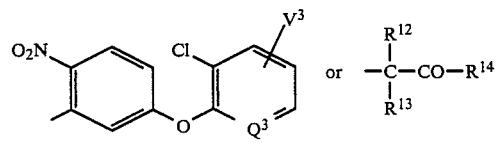

wherein $Q^2$, and $Q^3$ are each CH or N; $R^1$ and $R^2$ are each H, $C_1$-$C_5$ alkyl, $C_1$-$C_5$ alkoxy, or $C_2$-$C_6$ alkxoycarobnyl; $R^3$, $R^4$, and $R^5$ are each H or $C_1$-$C_5$ alkyl; $R^6$ is H, halogen, or $C_1$-$C_5$ alkyl; $R^7$, $R^8$, $R^9$, and $R^{10}$ are each H or $C_1$-$C_5$ alkyl; $R^{11}$ is H, $C_1$-$C_5$ alkyl, $C_1$-$C_5$ alkoxy, $C_2$-$C_6$ alkenyl, $C_6$-$C_{10}$ aryl, $C_7$-$C_{15}$ aryloxyalkyl, or $C_7$-$C_{15}$ aralkyl; $R^{12}$ and $R^{13}$ are each H or $C_1$-$C_5$ alkyl; $R^{14}$ is $C_1$-$C_5$ alkyl, $C_2$-$C_6$ alkenyl, $C_5$-$C_{10}$ aryl, or $C_7$-$C_{15}$ aralkyl; or $R^{13}$ and $R^{14}$ taken together form $C_3$-$C_4$ alkylene, $V^1$ and $V^2$ are each H, halogen, $NO_2$, CN, or $CF_3$; $V^3$ is halogen or $CF_3$; $W^1$ is —O— or —NH—; $W^2$ is —$(CH_2)_n$— wherein n is 0 or 1, or CO; $X^1$ is halogen, or a salt thereof, which is effective as a herbicidal agent.

3 Claims, No Drawings

HERBICIDALLY ACTIVE PHENOXYALKANECARBOXYLIC ACID DERIVATIVES

BACKGROUND OF THE INVENTION

1. Field of the Invention

The present invention relates to novel herbicidally active compounds (i.e., phenoaxyalkanecarboxylic acid derivatives) having the formula:

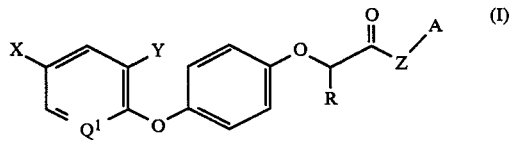

wherein $Q^1$ is CH or N; R is H or $C_1$–$C_5$ alkyl; X is H, halogen, $CF_3$, or $NO_2$; Y is H or halogen; Z is —O— or —NH—; A is

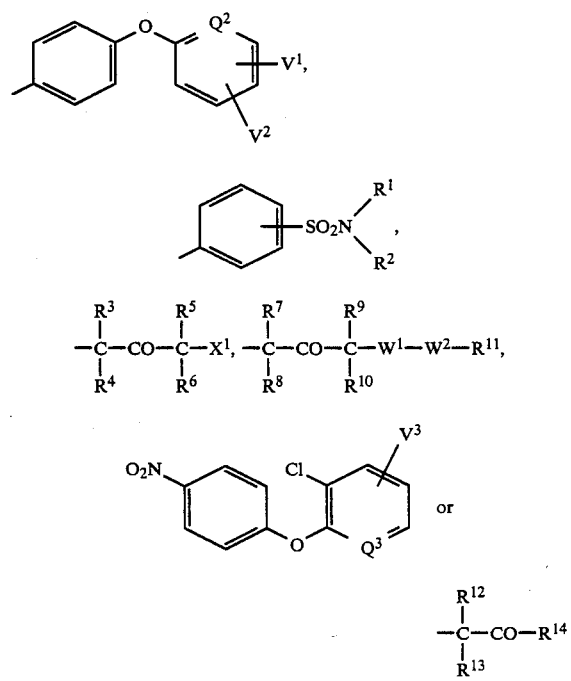

or

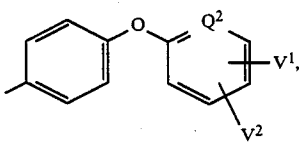

wherein $Q^2$ and $Q^3$ are each CH or N; $R^1$ and $R^2$ are each H, $C_1$–$C_5$ alkyl, $C_1$–$C_5$ alkoxy, or $C_2$–$C_6$ alkoxycarbonyl; $R^3$, $R^4$ and $R^5$ are each H or $C_1$–$C_5$ alkyl; $R^6$ is H, halogen, or $C_1$–$C_5$ alkyl; $R^7$, $R^8$, $R^9$, and $R^{10}$ are each H or $C_1$–$C_5$ alkyl; $R^{11}$ is H, $C_1$–$C_5$ alkyl, $C_1$–$C_5$ alkoxy, $C_2$–$C_6$ alkenyl $C_6$–$C_{10}$ aryl, $C_7$–$C_{15}$ aryloxyalkyl, or $C_7$–$C_{15}$ aralkyl; $R^{12}$ and $R^{13}$ are each H or $C_1$–$C_5$ alkyl; $R^{14}$ is $C_1$–$C_5$ alkyl, $C_2$–$C_6$ alkenyl, $C_6$–$C_{10}$ aryl, or $C_7$–$C_{15}$ aralkyl; or $R^{13}$ and $R^{14}$ taken together form $C_3$–$C_4$ alkylene; $V^1$ and $V^2$ are each H, halogen, $NO_2$, CN, or $CF_3$; $V^3$ is halogen or $CF_3$; $W^1$ is —O— or —NH—; $W^2$ is —$(CH_2)_n$— wherein n is 0 or 1, or —CO—; and $X^1$ is halogen; or a salt thereof.

These compounds (I) are useful as an effective ingredient for herbicides

2. Description of the Related Art

A series of α-(p-phenoxyphenoxy)propionic acid type and α-(p-pyridyloxyphenoxy)propionic acid type compounds have been developed as important herbicides in agriculture and horticulture. These α-(p-phenoxyphenoxy)propionic acid type and α-(p-pyridyloxyphenoxy)propionic acid type herbicides are safe in that they have little influence on useful plants to be harvested, compared with the phenoxy type herbicides formerly employed, and that they have a stronger herbicidal activity. But, these α-(p-phenoxyphenoxy)-propionic acid type and α-(p-pyridyloxyphenoxy)propionic acid type herbicides have a lower selectivity for plants of the rice family, causing drug damage to, for example, rice, wheat, and barley which are useful plants, and exhibit no effect on some perennial weeds, and therefore, they are extremely limited in, for example, application time and application methods.

SUMMARY OF THE INVENTION

Accordingly, an object of the present invention is to provide a novel compound (i.e., a phenoaxyalkanecarboxylic acid derivatives) having a herbicidal activity, which is a herbicide which will not cause drug damage to rice, wheat or barley, and having a high selectivity between the plants of the rice family, while maintaining the characteristics of the above-mentioned α-(p-phenoxyphenoxy)propionic acid type or α-(p-pyridyloxyphenoxy)propionic acid type herbicides, and a herbicide containing the phenoaxyalkanecarboxylic acid derivative.

Other objects and advantages of the present invention will be apparent from the following description.

In accordance with the present invention, there is provided a compound having the above-mentioned formula (I), or a salt thereof.

In accordance with the present invention, there is also provided a herbicide containing, as an effective ingredient, a herbicidally effective amount of a compound having the above-mentioned formula (I).

DESCRIPTION OF THE PREFERRED EMBODIMENTS

The present inventors, while studying the development of a herbicide not causing drug damage to rice, wheat, or barley and with an enhanced selectivity between monocotyledon plants, while maintaining the characteristics of these pyridyloxyphenoxy type herbicides, found a herbicidally active compound having the above-mentioned general formula (I), or a salt with thereof, with an extremely potent activity and good selectivity.

Examples of the above-mentioned salts are those of an inorganic acid such as hydrochloric acid, sulfuric acid, nitric acid, or phosphoric acid and those of an organic acid such as p-toluenesulfonic acid or methane sulfonic acid.

In the above-mentioned formula (I), when the substituent A is the resultant compound is an α-phenoxyalkanecarboxylic acid derivative having the formula:

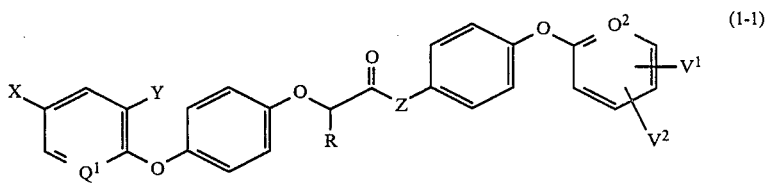

In the formula (1-1), wherein X is H, Cl, NO$_2$ and CF$_3$, and the halogen atom of the substituents Y, V$^1$ and V$^2$ may include, for example, fluorine, chlorine, bromine.

Examples of the lower alkyl group of R are methyl, ethyl, n-propyl, isopropyl, n-butyl, isobutyl, tert-butyl, and n-pentyl.

The present compound is different from the herbicides well known in the art, in that it contains an α-phenoxyalkanecarboxylic acid and a p-substituted phenol or a p-substituted aniline in the skelton thereof, and therefore, has a very low toxicity to the human body.

The α-phenoxyalkanecarboxylic acid derivative having the above formula (1-1) can be prepared according to the process as described below.

Thus, the α-phenoxyalkanecarboxylic acid derivative according to the present invention represented by the formula (1-1) can be obtained at high yield by allowing a carboxylic acid or a carboxylic acid derivative having the formula (2a-1):

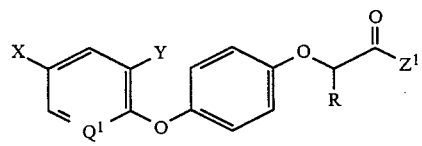

or

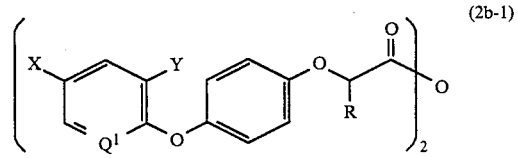

wherein Z$^1$ represents hydroxy group, a halogen atom or an active ester group, to react with a p-substituted phenol or p-substituted aniline of the formula (3-1):

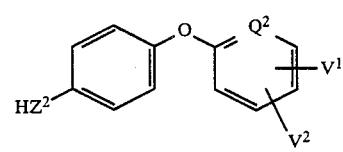

wherein Z$^2$ represents an oxygen atom or NH in the presence or absence of a base.

Examples of the suitable base are an alkali hydroxide or a trialkylamine.

The reaction conditions for the above reaction are not particularly limited, and the reaction can proceed in water or an organic solvent at room temperature or lower for 1 to 12 hours.

The compound of the present invention obtained as described above can be purified after completion of the reaction according to general purification methods.

Examples of these general purification methods include recrystallization, column chromatography, and thin layer chromatography.

In the above-mentioned formula (I), when the substituent A is

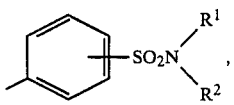

the resultant compound is an acylaminobenzenesulfonamide derivative having the formula:

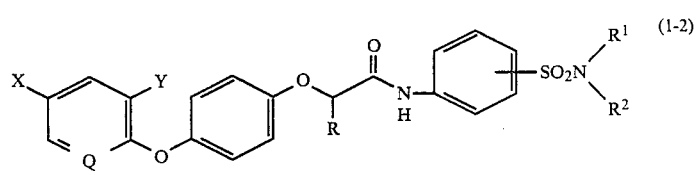

In the formula (1-2), wherein X is Cl and CF$_3$, and the halogen atom of the substituents Y may include fluorine, chlorine, and bromine.

Examples of the lower alkyl group R, R$^1$, and R$^2$ are methyl, ethyl, n-propyl, isopropyl, n-butyl, isobutyl, and the like.

Examples of the lower alkoxy group of R$^1$ and R$^2$ include methoxy, ethoxy, n-propoxy, isoproxy, n-butoxy, isobutoxy, and the like.

Examples of the lower alkoxycarbonyl group of R$^1$ and R$^2$ include methoxycarbonyl, ethoxycarbonyl, n-propoxycarbonyl, isopropoxycarbonyl, and the like.

The compound of the present invention is different from the herbicides well known in the art in that it contains an α-phenoxyalkanecarboxylic acid and aminobenzenesulfonamide in the skelton thereof, and therefore, has a very low toxicity to the human body.

The acylaminobenzenesulfonamide derivative having the above formula (1-2) can be prepared according to the process as described below.

Thus, the acylaminobenzenesulfonamide derivative according to the present invention represented by the formula (1-2) can be obtained at high yield by allowing a carboxylic acid or a carboxylic acid derivative having the formula (2a-1):

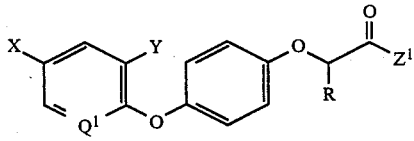

(2a-1)

or

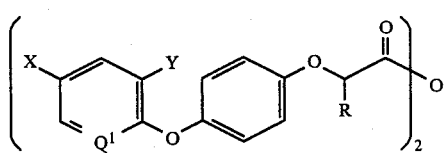

(2b-1)

wherein $Z^1$ represents hydroxy group, a halogen atom or an active ester group, to react with a p-substituted phenol or p-substituted aniline of the formula (3-2):

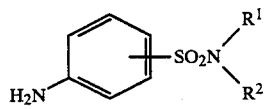

(3-2)

in the presence or absence of a base.

As the suitable base, for example, an alkali hydroxide or a trialkylamine can be used.

The reaction conditions for the above reaction are not particularly limited, and the reaction can proceed in water or an organic solvent at room temperature or lower for 1 to 12 hours.

The compound of the present invention obtained as described above can be purified after completion of the reaction according to general purification methods.

Examples of these general purification methods include recrystallization, column chromatography, and preparative thin layer chromatography.

In the above-mentioned formula (I), when the substituent A is

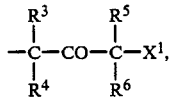

the resultant compound is an o-haloketone derivative having the formula (1-3):

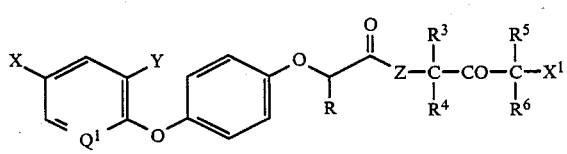

(1-3)

wherein X is $CF_3$, $X^1$ may include a fluorine, chlorine, bromine, or iodine. Representative of the lower alkyl group of the groups $R^3$, $R^4$, $R^5$ and $R^6$ are methyl, ethyl, n-propyl and isopropyl. Examples of the halogen atom of the group $R^6$ may include a fluorine, chlorine, bromine or iodine, and the lower alkyl group are represented by methyl, ethyl, n-propyl, and isopropyl groups.

The α-haloketone derivative represented by the above-mentioned formula (1-3) according to the present invention can be prepared according to the processes described below.

Preparation process 3-A

This process comprises allowing an amine salt of a compound having the formula (2-3):

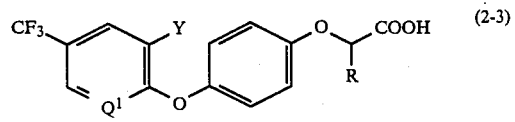

(2-3)

to react with a compound represented by the formula (3-3):

(3-3)

wherein $Z^3$ represents a halogen atom, $R^3$ and $R^4$ may be either identical or different and each represent a hydrogen atom or a lower alkyl group, and subsequently treating the compound formed of the formula (4-3):

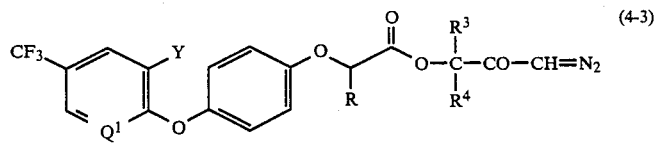

(4-3)

with a hydrogen halide or an aqueous hydrogen halide solution.

Preparation process 3-B

This process comprises allowing an amine salt of a compound having the above-mentioned formula (2-3) to react with a compound represented by the formula (5-3):

(5-3)

wherein $Z^3$ represents a halogen atom, $R^3$, $R^4$, and $R^5$ each independently represent a hydrogen atom or a $C_1$–$C_5$ lower alkyl group, $R^6$ represents hydrogen atom, a halogen atom or a $C_1$–$C_5$ lower alkyl group in a non-protonic polar solvent.

Preparation process C

This process comprises activating the carboxyl group of a compound having the formula (6-3):

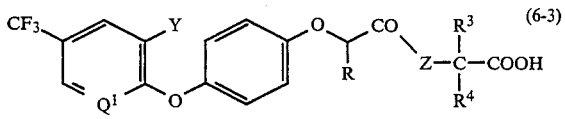

according to the acid halide method, the mixed acid anhydride method or the active esterification method, then allowing the activated compound to react with diazomethane, and subsequently, treating the reaction product with a hydrogen halide or an aqueous hydrogen halide solution.

As the amine to be used in the above preparation process A and the preparation process B, there may be included dialkylamines and trialkylamines, in general, but preferably dicyclohexylamine is used.

The non-protonic polar solvent in the preparation process A and the preparation process B is not particularly limited, but preferable examples include dimethylformamide and dimethylsulfoxide.

The condensation reactions of the above-mentioned preparation processes A and B may be generally conducted at a temperature of 0° C. to 100° C., preferably room temperature to 60° C. On the other hand, the halogenation reaction in the above preparation processes A and C is generally conducted at −20° C. to 40° C., preferably at 0° C. to room temperature. Further, the temperature for carrying out the diazomethylation reaction in the above preparation process C may be generally −20° C. to 30° C., preferably 0° C. to 5° C.

The reaction is generally completed within 0.1 to 3 hours.

The compound of the present invention obtained as described above can be purified by general purification methods, if desired. Examples of these general purification methods may include recrystallization, column chromatography, and thin layer chromatography.

In the compounds according to the present invention, optical isomers based on R, $R^3$, $R^4$, $R^5$, $R^6$ and $X^1$ exist, and all of these are also included within the scope of the present invention.

In the above-mentioned formula (I), when the substituent A is

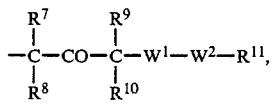

the resultant compound is an α-substituted ketone derivative having the formula (1-4):

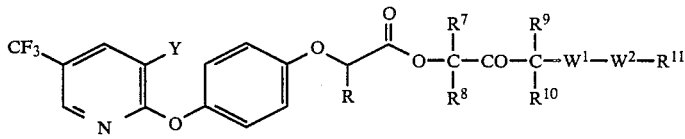

In the above formula (1-4), representative of the lower alkyl groups represented by the groups $R^7$, $R^8$, $R^9$, and $R^{10}$, are alkyl groups having 1 to 5 carbon atoms such as methyl, ethyl, n-propyl, isopropyl, n-butyl, and isobutyl groups, and representative examples of the lower alkyl group represented by $R^{11}$ include alkyl groups having 1 to 5 carbon atoms such as methyl, ethyl, n-propyl, isopropyl, n-butyl, isobutyl, and tert-butyl, or halo-substituted alkyl groups such as chloroethyl, chloropropyl, bromoethyl, bromopropyl, trifluoromethyl, and trifluoroethyl groups. Representative of the lower alkoxy group are alkoxy groups having 1 to 5 carbon atoms such as methoxy, ethoxy, n-propyloxy, and tert-butoxy groups; representative of the lower alkenyl group are alkenyl groups having 2 to 4 carbon atoms, such as vinyl, allyl groups, or substituted alkenyl groups substituted with halogens; representative of the aryl group are aryl groups having 6 to 10 carbon atoms, such as phenyl, p-chlorophenyl, and tolyl groups, and substituted derivatives thereof substituted with halogens; representative of the aryloxyalkyl group are aryloxyalkyl groups having 7 to 10 carbon atoms, such as phenoxymethyl and p-chlorophenoxyethyl groups and substituted derivatives thereof substituted with halogens; and representative of the aralkyl group are aralkyl groups having 7 to 10 carbon atoms, such as phenethyl and phenylpropyl groups and substituted derivatives thereof substituted with halogens.

The compound of the above formula (1-4) according to the present invention is different from the herbicides well known in the art in that it contains pyridyloxyphenoxypropionic acid and an α-substituted ketone derivative in the skelton thereof, and has an extremely low toxicity to the human body.

The α-substituted ketone derivative having the above-mentioned formula (1-4) of the present invention can be prepared as described below.

Preparation process 4-A

An amine salt of a compound of the formula:

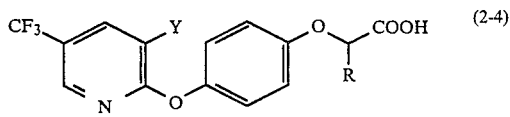

is allowed to react with a compound of the formula:

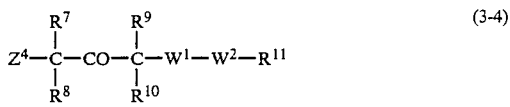

wherein $Z^4$ represents a chlorine atom or bromine atom, $W^1$ represents an oxygen atom or imino group, $W^2$ represents a single bond or carbonyl group, $R^{11}$ represents a hydrogen atom, a lower alkyl group, a lower alkoxy group, a lower alkenyl group, an aryloxyaralkyl group or an aralkyl group, which may be each substituted in a non-protonic polar solvent.

Preparation process 4-B

An amine salt of a compound of the formula (2-4) is allowed to react with a compound of the formula (4-4):

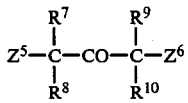  (4-4)

wherein $Z^5$ and $Z^6$ may be identical or different, and represent a chlorine atom or bromine atom, and $R^7 R^8$, $R^9$, $R^{10}$, and are as defined above in a non-protonic polar solvent to derive a compound of the formula:

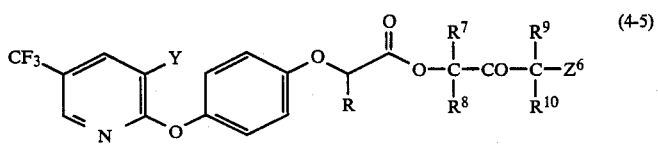  (4-5)

and subsequently, this reaction product is allowed to react with an amine salt of a carboxylic acid having the formula:

  $R^{11}$—COOH  (4-6)

(wherein $R^{11}$ is as defined above) in a non-protonic polar solvent.

As the amine to be used in the above-mentioned preparation process 4-A and the preparation process 4-B, there may be included dialkylamines, trialkylamines, in general, but preferably dicyclohexylamine is used.

The non-protonic polar solvent in the preparation process 4-A and the preparation process 4-B is not particularly limited, but preferable examples include dimethylformamide, dimethylsulfoxide. The condensation reactions of the above preparation process 4-A and the preparation process 4-B may be generally conducted at a temperature of 0° C. to 100° C., preferably room temperature to 60° C. The reaction is generally completed within 0.1 to 3 hours.

The compound (1-4) of the present invention obtained as described above can be purified by general purification methods, if desired. Examples of these general purification methods include recrystallization, column chromatography, and thin layer chromatography.

In the compounds according to the present invention, optical isomers based on the above substituents $R^7$, $R^8$, $R^9$, $R^{10}$, and $W^1$ and pyridyloxyphenoxypropionic acid exist, and all of these are also included within the scope of the present invention.

The compounds of the present invention thus obtained have a low toxicity to the human body and domestic animals, and have an extremely specific and potent growth controlling activity for monocotiledon plants. This suggests that the compounds of the present invention can be widely used as herbicides.

In the formula (I), when the substituent A is

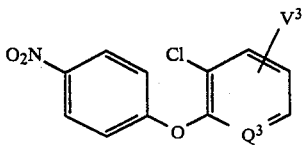

the resultant compound is a phenoxyalkane carboxylic acid derivative having the formula (1-5):

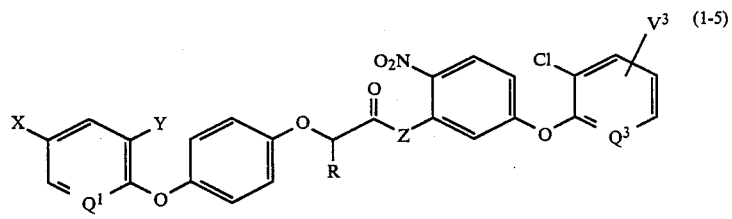  (1-5)

In the formula (1-5), examples of the alkyl group R are methyl, ethyl, n-propyl, and isopropyl, and the halogen atom of $V^3$ is chlorine, bromine, fluorine, or iodine.

The present compound is different from the herbicides well known in the art in that it contains a phenoxyalkanecarboxylic acid and nitrophenol or nitroaniline in the skelton thereof, and therefore, has a very low toxicity to the human body.

The phenoxyalkanecarboxylic acid derivative having the above formula (1-5) can be prepared according to the process as described below.

Thus, the phenoxyalkanecarboxylic acid derivative according to the present invention having the formula (1-5) can be obtained at a high yield by allowing a carboxylic acid or a carboxylic acid derivative having the formula (2a-5) or (2b-5):

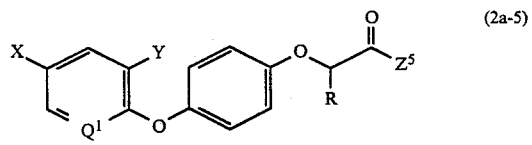  (2a-5)

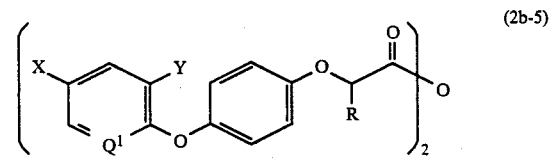  (2b-5)

wherein $Z^5$ represents hydroxyl, halogen, or an active ester group, to react with nitrophenol or nitroaniline having the formula (3-5):

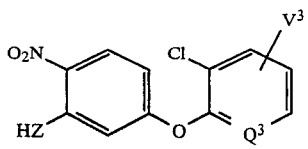 (3-5)

in the presence or absence of a base.

As the suitable base, for example, an alkali hydroxide or an organic amine such as a trialkylamine or pyridine can be used.

The reaction conditions for the above reaction are not particularly limited, and the reaction can proceed in water or an organic solvent at room temperature or lower for 1 to 12 hours.

The present compound obtained as described above can be purified after completion of the reaction according to general purification methods.

Examples of these general purification methods include recrystallization, column chromatography, and thin layer chromatography.

In the compounds according to the present invention, optical isomers based on the one asymmetric carbon atom exist, and all of these are also included within the scope of the present invention.

The present compounds thus obtained have a low toxicity to the human body and domestic animals, and have an extremely specific and potent growth controlling activity for monocotiledon plants. This suggests that the compounds of the present invention can be widely used as herbicides.

In the formula (I), when the substituent A is

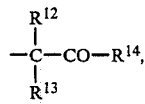

the resultant compound is an α-substituted ketone derivative having the formula (1-6):

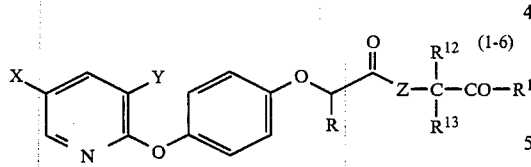 (1-6)

The α-substituted ketone derivative having the above-mentioned formula (1-6) according to the present invention can be prepared according to the processes as described below.

Thus, the α-substituted ketone derivative according to the present invention having the formula (1-6) can be obtained by allowing an amine salt of a compound having the formula (2-6):

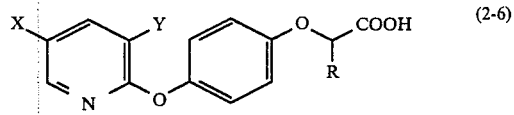 (2-6)

to react with a compound having the formula (3-6):

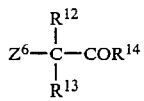 (3-6)

wherein $Z^6$ represents halogen.

Examples of the amines usable in the above reaction are dialkylamines and trialkylamines, but preferably, dicyclohexylamine is used. The reaction is usually carried out in an aprotic solvent. Examples of such solvents are dimethylformamide and dimethylsulfoxide. The reaction temperature is generally 0° C. to 100° C., preferably room temperature to 60° C. The reaction is generally completed in 0.1 to 3 hours.

The present compound obtained as described above can be purified after completion of the reaction according to general purification methods.

Examples of these general purification methods include recrystallization, column chromatography, and thin layer chromatography.

In the compounds according to the present invention, optical isomers based on the two asymmetric carbon atoms exist, and all of these are also included within the scope of the present invention.

The present compounds thus obtained have a low toxicity to the human body and domestic animals, and have an extremely specific and potent growth controlling activity for monocotiledon plants. This suggests that the compounds of the present invention can be widely used as herbicides.

The compounds of the present invention as the herbicide can be generally applied while mixed with suitable carriers, for example, solid carriers such as clay, diatomaceous earth, or liquid carriers such as water, alcohols, aromatic hydrocarbons, ethers, ketones, and esters. Also, if desired, they can be provided in a form such as an emulsion, wettable agent, powder, granule, may be added with an emulsifier, dispersing agent, suspending agent, spreading agent, stabilizer, and may be applied as a mixture with various kinds of herbicides, various pesticides, germicides, plant growth controllers.

In the practice of the present invention, the concentration of the compound of the present invention can be widely varied, but preferably is in the range of 0.5 to 10 g per 10 ares. The various preparations described above can be prepared so as to contain 0.5% to 90% by weight of the active ingredient.

EXAMPLES

The present invention now will be further illustrated by, but is by no means limited to, the following Reference Examples, Synthesis Examples, and Test Examples.

REFERENCE EXAMPLE 1: SYNTHESIS OF THE STARTING MATERIAL HAVING THE FORMULA (2a-1)

(A) 2-(4-(4-Chlorophenoxy)phenoxy)propionic acid chloride:

4-Bromochlorobenzene (3.8 g), hydroquinone monomethyl ether (3.1 g) and potassium hydroxide (1.5 g) and copper powder (0.1 g) were mixed and the reaction was carried out at 160° C. to 200° C. for 3 hours. After cooling to room temperature, the reaction mixture was extracted with benzene (100 ml) and washed with 1N sodium hydroxide, water, and saturated aqueous sodium chloride. After drying over anhydrous magnesium sulfate, the solvent was evaporated under a reduced pressure and the residue was purified by medium pressure column chromatography using silica gel, to obtain 4-(4-chlorophenoxy)phenol methyl ether (2.5 g).

The methyl ether obtained (2.5 g) was dissolved in dry methylene chloride (20 ml), the solution was added to a solution of boron tribromide (3.0 g) in dry methylene chloride (20 ml), and the mixture was stirred at room temperature for 2 hours. After an addition of water, the mixture was extracted with ether (100 ml) and the extract was dried over anhydrous magnesium sulfate, followed by evaporation of the solvent to obtain 4-(4-chlorophenoxy)phenol (2.4 g).

The phenol obtained (1.8 g) and sodium hydroxide (0.7 g) were dissolved in water (10 ml), and the solution was heated after an addition of 2-bromopropionic acid (1.2 g), and then evaporated to dryness. The residue was dissolved in water (20 ml), washed with ether (20 ml), then made acidic with an addition of 1N hydrochloric acid and extracted with ether (50 ml). The extract was dried over anhydrous magnesium, and the solvent was evaporated under a reduced pressure to obtain 2-(4-(4-chlorophenoxy)propionic acid (1.1 g) (m.p. 115° C.-117° C.).

The carboxylic acid (0.9 g) was dissolved in dry benzene (10 ml) and refluxed, after an addition of thionyl chloride (5 ml), for 2 hours. The solvent and thionyl chloride were than evaporated under a reduced pressure to obtain 2-(4-(chlorophenoxy)phenoxy)propionic acid chloride (1.0 g).

(a) 2-bromoacetic acid, (b) 2-bromobutyric acid, and (c) 2-bromovaleric acid in the above (A), were used to obtain (a'), 4-(4-chlorophenoxy)phenoxyacetic acid chloride, (b') 2-(4-(4-chlorophenoxy)phenoxybutyric acid chloride, (c') 2-(4-(4-chlorophenoxy)phenoxy)valeric acid chloride, respectively. Also, by using (d) 4-bromonitrobenzene instead of 4-bromochlorobenzene in the above (a), (d') 2-(4-(4-nitrophenoxy)phenoxy)propionic acid chloride was obtained.

Also, by using a commercially available 4-phenoxyphenol instead of 4-(4-chlorophenoxy)phenol, 2-(4-phenoxyphenoxy)propionic acid chloride was obtained.

(B)
2-(4-(3-Chloro-5-trifluoromethyl-2-pyridyloxy)phenoxypropionic acid chloride hydrochloride:

Ethyl 2-bromopropionate (36.2 g) and hydroquinone monobenzyl ether (40.0 g) were dissolved in dry dimethyl sulfoxide (100 ml), and pulverized potassium hydroxide (11.2 g) was added to the resultant solution. After stirring at room temperature for 20 hours, the reaction mixture was poured into ice-water (500 ml) and extracted with ethyl acetate (500 ml×2). The extract was washed with 1N hydrochloric acid, water, and saturated aqueous sodium chloride, dried over anhydrous magnesium sulfate, and the residue obtained by evaporation of the solvent under a reduced pressure was purified by medium pressure column chromatography using silica gel, to obtain ethyl 2-(4-benzyloxyphenoxy)propionate (57.3 g).

The benzyl ether (57.3 g) was dissolved in ethanol (100 ml), the benzyl group was removed by catalytic reduction with an addition of palladium-carbon (6.0 g), and the solvent was evaporated to obtain ethyl 2-(4-hydroxyphenoxy)propionate.

The phenol (21.0 g) and 2,3-dichloro-5-trifluoromethyl pyridine (21.6 g) were dissolved in dry dimethyl sulfoxide (150 ml), and anhydrous potassium carbonate (13.8 g) was added to the resultant solution, followed by stirring at 100° C. for 3 hours. The reaction mixture was poured into ice-water (300 ml), extracted with ethyl acetate (300 ml×2), and the extract was washed with 1N hydrochloric acid, water, and saturated aqueous sodium chloride, and dried over anhydrous magnesium sulfate. The residue obtained by evaporation of the solvent under a reduced pressure was purified by medium pressure column chromatography using silica gel, to obtain ethyl 2-(4-(3-chloro-5-trifluoromethyl-2-pyridyloxy)phenoxy)propionate (31.0 g).

The ester (25.0 g) was dissolved in methanol (100 ml) added with 1N sodium hydroxide (77 ml), and the reaction was carried out at room temperature for 3 hours. Methanol was evaporated under a reduced pressure, the residue was washed with ether (200 ml), and then made acidic with addition of 1N hydrochloric acid and extracted with ether (200 ml×2). After drying over anhydrous magnesium sulfate, the solvent was evaporated under a reduced pressure to obtain 2-(4-(3-chloro-5-trifluoromethyl-2-pyridyloxy)phenoxy)propionic acid (20.5 g) (m.p. 108° C.-110° C.).

The carboxylic acid (1.5 g) was dissolved in dry benzene (10 ml) and refluxed, with an addition of thionyl chloride (5 ml), for 2 hours. Evaporation of the solvent and thionyl chloride gave 2-(4-3-chloro-5-trifluoromethyl-2-pyridyloxy)phenoxy)propionic acid chloride hydrochloride (1.5 g).

By using 2-chloro-5-trifluoromethylpyridine instead of 2,3-dichloro-5-trifluoromethylpyridine in the above (b), 2-(4-(5-trifluoromethyl-2-pyridyloxy)phenoxy)propionic acid chloride hydrochloride was obtained.

REFERENCE EXAMPLE 2: SYNTHESIS OF THE STARTING MATERIAL HAVING THE FORMULA (3-1)

(A) 4-(4-Nitrophenoxy)phenol:

4-Bromonitrobenzene (4.0 g), hydroquinone monomethyl ether (3.1 g), potassium hydroxide (1.5 g) and copper powder (0.1 g) were mixed and the reaction was carried out at 160° C. to 200° C. for 3 hours. After cooling to room temperature, the reaction mixture was extracted with benzene (100 ml), and the extract was washed with 1N sodium hydroxide, water, and saturated aqueous sodium chloride. After drying over magnesium sulfate, the solvent was evaporated under a reduced pressure and the residue obtained was purified by medium pressure column chromatography using silica gel, to obtain 4-(4-nitrophenoxy)phenol methyl ether (1.5 g).

The methyl ether obtained (0.4 g) was dissolved in dry methylene chloride (5 ml), and the resultant solution was added to a solution of boron trifluoride (0.5 g) in dry methylene chloride (5 ml), followed by stirring at room temperature for 2 hours. After an addition of water, the mixture was extracted with ether (30 ml) and dried over anhydrous magnesium sulfate to obtain 4-(4-nitrophenoxy)phenol (0.4 g) (m.p. 172.9° C.-173.5° C.).

In the above (A), instead of 4-bromonitrobenzene, (a) 2-bromonitrobenzene, (b) 2,4-dichloronitrobenzene, (c) 3,4-dichloronitrobenzene, (d) 4-bromochlorobenzene, (e) 4-bromocyanobenzene, (a') 4-(2-nitrophenoxy)phenol (m.p. 103° C.-105° C.), (b') 4-(3-chloro-4-nitrophenoxy)phenol (m.p. 113° C.–115° C.), (c') 4-(2-chloro-4-nitrophenoxy)phenol (m.p. 149° C.–151° C.), (d') 4-(4-chlorophenoxy)phenol (m.p. 81.5° C.–83.5° C.), (e') 4-(4-cyanophenoxy)phenol (m.p. 148.5° C.–149.5° C.) were obtained respectively.

Also, according to the same method, by using 2-bromo-3-chloro-5-trifluoromethylpyridine, 4-(3-chloro-5-trifluoromethyl-2-pyridyloxy)phenol was obtained.

(B) 4-(4-Nitrophenoxy)aniline:

p-Acetoaminophenol (1.5 g) and 4-bromonitrobenzene (2.0 g) were dissolved in dry dimethyl sulfoxide (15 ml) and anhydrous potassium carbonate (1.4 g) was added, followed by stirring at 100° C. for 3 hours. The reaction mixture was poured into ice-water (30 ml), extracted with ethyl acetate (30 ml×2), and the extract was washed with 1N hydrochloric acid, water, and saturated aqueous sodium chloride, followed by drying over anhydrous magnesium sulfate. The residue obtained by evaporation of the solvent under a reduced pressure was purified by medium pressure column chromatography using silica gel, to obtain 4-(4-nitrophenoxy)acetanilide (2.0 g).

The acetanilide (1.9 g) was dissolved in methanol (5 ml), and refluxed, with an addition of 4N hydrochloric acid (7 ml), for 1 hour. After cooling to room temperature, methanol was evaporated under a reduced pressure, and the residue was made basic with an addition of 1N sodium hydroxide and extracted with ethyl acetate (30 ml×2). After drying over anhydrous sodium sulfate, the solvent was evaporated under a reduced pressure to obtain 4-(4-nitrophenoxy)aniline (1.6 g) (m.p. 132.5° C.–134° C).

In the above (B), 4-bromonitrobenzene was replaced with 2,3-dichloro-5-trifluoromethylpyridine to obtain 4-(3-chloro-5-trifluoromethyl-2-pyridyloxy)aniline.

EXAMPLE 1-1

4-(4-Nitrophenoxy)phenyl 2-(4-(4-chlorophenoxy)phenoxy)propionate 2-(4-(4-Chlorophenoxy)phenoxy)propionic acid chloride (0.6 g) and 4-(4-nitrophenoxy)phenol (0.5 g) were dissolved in dry tetrahydrofuran (10 ml), and the solution was stirred with an addition of triethylamine (0.3 ml) at room temperature for 2 hours. After completion of the reaction, the solvent was evaporated under a reduced pressure, the residue was dissolved in methylene chloride (20 ml), and washed with 1N hydrochloric acid, water, saturated aqueous sodium hydrogen carbonate, water, and aqueous saturated sodium chloride. After drying over anhydrous magnesium sulfate, the solvent was evaporated and the residue obtained was purified by medium pressure column chromatography to obtain 4-(4-nitrophenoxy)phenyl 2-(4-(4-chlorophenoxy)phenoxy)propionate (0.8 g)

EXAMPLE 1-2

4-(2-Nitrophenoxy)phenyl 2-(4-(4-chlorophenoxy)phenoxy) propionate

In Example 1-1, by using 4-(2-nitrophenoxy)phenol instead of the 4-(4-nitrophenoxy)phenol used in Example 1-1, 4-(2-nitrophenoxy)phenyl 2-(4-(4-chlorophenoxy)phenoxy)propionate was obtained.

EXAMPLE 1-3

4-(3-Chloro-4-nitrophenoxy)phenyl 2-(4-(4-chlorophenoxy)phenoxy)propionate

In Example 1-1, by using of 4-(3-chloro-4-nitrophenoxy)phenol instead of the 4-(4-nitrophenoxy)phenol used in Example 1-1, 4-(3-chloro-4-nitrophenoxy)phenyl 2-(4-(4-chlorophenoxy)phenoxy)propionate was obtained.

EXAMPLE 1-4

4-(2-Chloro-4-nitrophenoxy)phenyl 2-(4-(4-chlorophenoxy)phenoxy)propionate

In Example 1-1, by using of 4-(2-chloro-4-nitrophenoxy)phenol instead of the 4-(4-nitrophenoxy)phenol used in Example 1-1, 4-(2-chloro-4-nitrophenoxy)phenyl 2-(4-(4-chlorophenoxy)phenoxy)propionate was obtained.

EXAMPLE 1-5

4-(4-Chlorophenoxy)phenyl 2-(4-(4-chlorophenoxy)phenoxy)propionate

In Example 1-1, by using of 4-(4-chlorophenoxy)phenol instead of the 4-(4-nitrophenoxy)phenol used in Example 1-1, 4-(4-chlorophenoxy)phenyl 2-(4-(4-chlorophenoxy)phenoxy)propionate was obtained.

EXAMPLE 1-6

4-(4-Cyanophenoxy)phenyl 2-(4-(4-chlorophenoxy)phenoxy)propionate

In Example 1-1, by using of 4-(4-cyanophenoxy)phenol instead of the 4-(4-nitrophenoxy)phenol used in Example 1-1, 4-(4-cyanophenoxy)phenyl 2-(4-(4-chlorophenoxy)phenoxy)propionate was obtained.

EXAMPLE 1-7

4-Phenoxyphenyl 2-(4-(4-chlorophenoxy)phenoxy propionate

In Example 1-1, by using of 4-phenoxyphenol instead of the 4-(4-nitrophenoxy)phenol used in Example 1-1, 4-phenoxyphenyl 2-(4-(4-chlorophenoxy)phenoxy)propionate was obtained.

EXAMPLE 1-8

4-(4-Nitrophenoxy)phenyl 4-(4-chlorophenoxy)phenoxyacetate

In Example 1-1, by using 4-(4-chlorophenoxy)phenoxyacetic acid chloride instead of 2-(4-(4-chlorophenoxy)pheoxy)propionic acid chloride, 4-(4-nitrophenoxy)phenyl 4-(4-chlorophenoxy)phenoxyacetate was obtained.

EXAMPLE 1-9

4-(4-Nitrophenoxy)phenyl 2-(4-(4-chlorophenoxy)phenoxy)butyrate

In Example 1-1, by using 2-(4-(4-chlorophenoxy)phenoxy)butyric acid chloride instead of 2-(4-(4-chlorophenoxy)phenoxy)propionic acid chloride, 4-(4nitrophenoxy)phenyl 2-(4-(4-chlorophenoxy)phenoxy)butyrate was obtained.

EXAMPLE 1-10

4-(4-Nitrophenoxy)phenyl 2-(4-(4-chlorophenoxy)phenoxy)valerate

In Example 1-1, by using 2-(4-(4-chlorophenoxy)phenoxy)valeric acid chloride instead of 2-(4-(4chlorophenoxy)phenoxy)propionic acid chloride, 4-(4-nitrophenoxy)phenyl 2-(4-(4-chlorophenoxy)phenoxy)valerate was obtained.

EXAMPLE 1-11

4-(4-Nitrophenoxy)phenyl 2-(4-(4-nitrophenoxy)phenoxy)propionate

In Example 1-1, by using 2-(4-(4-nitrophenoxy)phenoxy)propionic acid chloride instead of 2-(4-(4-chlorophenoxy)phenoxy)propionic acid chloride, 4-(4-nitrophenoxy)phenyl 2-(4-(4-nitrophenoxy)phenoxy)propionate was obtained.

EXAMPLE 1-12

4-(4-Nitrophenoxy)phenyl 2-(4-4-phenoxyphenoxy)phenoxy)propionate

In Example 1-1, by using 2-(4-(4-phenoxyphenoxy)phenoxy)propionic acid chloride instead of 2-(4-(4-chlorophenoxy)phenoxy)propionic acid chloride, 4-(4-phenoxyphenoxy)phenyl 2-(4-(4-nitrophenoxy)phenoxy)propionate was obtained.

EXAMPLE 1-13

4-(4-Nitrophenoxy)phenyl 2-(4-(3-chloro-5-trifluoromethyl-2-pyridyloxy)phenoxy)propionate 2-(4-(3-Chloro-5-trifluoromethyl-2-pyridyloxy)phenoxypropionic acid chloride hydrochloride (0.7 g) and 4-(4-nitrophenoxy)phenol (0.5 g) were dissolved in dry tetrahydrofuran (10 ml), and stirred with an addition of triethylamine (0.5 ml) at room temperature for 2 hours. After completion of the reaction, the solvent was evaporated under a reduced pressure and the residue was dissolved in methylene chloride (20 ml), followed by washing with 1N hydrochloric acid, water, saturated aqueous sodium hydrogen carbonate, water and saturated aqueous sodium chloride. After drying over anhydrous magnesium sulfate, the solvent was evaporated under a reduced pressure and the residue obtained was purified by medium pressure column chromatography by using silica gel, to obtain 4-(4-nitrophenoxy)phenyl 2-(4-(3-chloro-5-trifluoromethyl-2-pyridyloxy)phenoxy)propionate (0.9 g) (oily product).

EXAMPLE 1-14

4-(2-Nitrophenoxy)phenyl 2-(4-(3-chloro-5-trifluoromethyl-2-pyridyloxy)phenoxy)propionate In Example 1-13, by using 4-(2-nitrophenoxy)phenol instead of 4-(4-nitrophenoxy)phenol, 4-(2-nitrophenoxy)phenyl 2-(4-(3-chloro-5-trifluoromethyl-2-pyridyloxy)phenoxy)propionate was obtained.

EXAMPLE 1-15

4-(3-Chloro-4-nitrophenoxy)phenyl 2-(4-(3-chloro5-trifluoromethyl-2-pyridyloxy)phenoxy)propionate In Example 1-13, by using 4-(3-chloro-4-nitrophenoxy)phenol instead of 4-(4-nitrophenoxy)phenol, 4-(3-chloro-4-nitrophenoxy)phenyl 2-(4-(3-chloro-5-trifluoromethyl-2-pyridyloxy)phenoxy)propionate was obtained.

EXAMPLE 1-16

4-(2-Chloro-4-nitrophenoxy)phenyl 2-(4-(3-chloro-5-trifluoromethyl-2-pyridyloxy)phenoxy)propionate In Example 1-13, by using 4-(2-chloro-4-nitrophenoxy)phenol instead of 4-(4-nitrophenoxy)phenol, 4-(2-chloro-4-nitrophenoxy)phenyl 2-(4-(3-chloro-5-trifluoromethyl-2-pyridyloxy)phenoxy)propionate was obtained.

EXAMPLE 1-17

4-(3-Chloro-5-trifluoromethyl-2-pyridyloxy))phenyl 2-(4-(3-chloro-5-trifluoromethyl-2-pyridyloxy)phenoxy)propionate In Example 1 - 13, by using 4-(3-chloro-5-trifluoromethyl-2-pyridyloxy)phenol instead of 4-(4-nitrophenoxy)phenol, 4-(3-chloro-5-trifluoromethyl-2-pyridyloxy)phenyl 2-(4-(3-chloro-5-trifluoromethyl-2-pyridyloxy)phenoxy)propionate was obtained.

EXAMPLE 1-18

4-(2-(4-(3-Chloro-5-trifluoromethyl)-2-pyridyloxy)phenoxy)propionyl)amino-(4-nitrophenoxy)benzene In Example 1-13, by using 4-(4-nitrophenoxy)aniline instead of 4-(4-nitrophenoxy)phenol, 4-(2-(4-(3-chloro-5-trifluoromethyl)-2-pyridyloxy)phenoxy)propionyl)amino-(4-nitrophenoxy)benzene was obtained.

EXAMPLE 1-19

4-(2-(4-(3-Chloro-5-trifluoromethyl)-2-pyridyloxy)phenoxy)propionyl)amino-(3-chloro-5-trifluoromethyl-2-pyridyloxy)benzene In Example 1-13, by using 4-(3-chloro-5-trifluoromethyl-2-pyridyloxy)aniline instead of 4-(4nitrophenoxy)phenol, 4-(2-(4-(3-chloro-5-trifluoromethyl)-2-pyridyloxy)phenoxy)propionyl)amino-(3-chloro-5-trifluoromethyl-2-pyridyloxy)benzene was obtained.

EXAMPLE 1-20

4-(4-Nitrophenoxy)phenyl 2-(4-(5-trifluoromethyl-2-pyridyloxy)phenoxy)propionate In Example 1-13, by using 2-(4-(5-trifluoromethyl-2-pyridyloxy)phenoxy)propionic acid chloride hydrochloride instead of 2-(4-(3-chloro-5-trifluoromethyl-2-pyridyloxy)phenoxypropionic acid chloride hydrochloride, 4-(4-nitrophenoxy)phenyl 2-(4-(5-trifluoromethyl-2-pyridyloxy)phenoxy)propionate was obtained.

EXAMPLE 1-21

4-(2-Nitrophenoxy)phenyl 2-(4-(5-trifluoromethyl-2-pyridyloxy)phenoxy)propionate In Example 1-13, by using 2-(4-5-trifluoromethyl-2-pyridyloxy)phenoxy)propionic acid chloride hydrochloride instead of 2-(4-(3-chloro-5-trifluoromethyl-2-pyridyloxy)phenoxypropionic acid chloride hydrochloride, and 4-(2-nitrophenoxy)phenol instead of 4-(4-nitrophenoxy)phenol, 4-(4-nitrophenoxy)phenyl 2-(4-(5-trifluoromethyl-2-pyridyloxy)phenoxy)propionate was obtained.

EXAMPLE 1-22

4-(3-Chloro-4-nitrophenoxy)phenyl 2-(4-(5-trifluoromethyl-2-pyridyloxy)phenoxy)propionate In Example 1-13, by using 2-(4-(5-trifluoromethyl-2-pyridyloxy)phenoxy)propionic acid chloride hydrochloride instead of 2-(4-(3-chloro-5-trifluoromethyl-2-pyridyloxy)phenoxy)propionic acid chloride hydrochloride, and 4-(3-chloro-4-nitrophenoxy)phenyl-2-(4-(5-trifluoromethyl-2-pyridyloxy)phenoxy)propionate was obtained.

EXAMPLE 1-23

4-(2-Chloro-4-nitrophenoxy)phenyl 2-(4-(5-trifluoromethyl-2-pyridyloxy)phenoxy)propionate In Example 1-13, by using 2-(4-(5-trifluoromethyl-2-pyridyloxy)phenoxy)propionic acid chloride hydrochloride instead of 2-(4-(3-chloro-5-trifluoromethyl-2-pyridyloxy)phenoxy)propionic acid chloride hydrochloride, and 4-(2-chloro-4-nitrophenoxy)phenol instead of 4-(4-nitrophenoxy)phenol, 4-(2-chloro-4-nitrophenoxy)phenyl 2-(4-(5-trifluoromethyl-2-pyridyloxy)phenoxy)propionate was obtained.

The physicochemical data of the compounds obtained is shown in Table 1.

TABLE 1

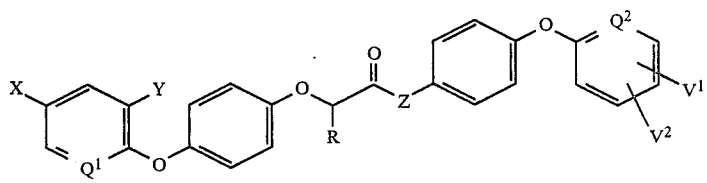

| Example No. | $Q^1$ | $Q^2$ | X | Y | R | Z | $V^1, V^2$ | Properties | NMR Spectrum/δ ppm (J/Hz) | Yield (%) |
|---|---|---|---|---|---|---|---|---|---|---|
| 1-1 | CH | CH | Cl | H | $CH_3$ | O | 4-$NO_2$, H | Oily substance | ($CDCl_3$) 1.77(3H, d, J=6.6), 4.92(1H, q, J=6.6), 6.73–8.17(16H, m) | 79 |
| 1-2 | CH | CH | Cl | H | $CH_3$ | O | 2-$NO_2$, H | " | ($CDCl_3$) 1.77(3H, d, J=6.6), 4.91(1H, q, J=6.6), 6.72–7.94(16H, m) | 79 |
| 1-3 | CH | CH | Cl | H | $CH_3$ | O | 4-$NO_2$, 3-Cl | " | ($CDCl_3$) 1.77(3H, d, J=7.2), 4.90(1H, q, J=7.2), 6.72–7.94(15H, m) | 74 |
| 1-4 | CH | CH | Cl | H | $CH_3$ | O | 4-$NO_2$, 2-Cl | " | ($CDCl_3$) 1.83(3H, d, J=7.2), 4.96(1H, q, J=7.2), 6.77–8.33(15H, m) | 77 |
| 1-5 | CH | CH | Cl | H | $CH_3$ | O | 4-Cl, H | " | ($CDCl_3$) 1.76(3H, d, J=7.2), 4.89(1H, q, J=7.2), 6.72–7.30(16H, m) | 79 |
| 1-6 | CH | CH | Cl | H | $CH_3$ | O | 4-CN, H | Oily substance | ($CDCl_3$) 1.77(3H, d, J=6.6), 4.92(1H, q, J=6.6), 6.73–7.60(16H, m) | 85 |
| 1-7 | CH | CH | Cl | H | $CH_3$ | O | H, H | " | ($CDCl_3$) 1.76(3H, d, J=7.2), 4.87(1H, q, J=7.2), 6.72–7.26(17H, m) | 88 |
| 1-8 | CH | CH | Cl | H | H | O | 4-$NO_2$, H | " | ($CDCl_3$) 4.84(2H, S), 6.73–8.22(16H, m) | 62 |
| 1-9 | CH | CH | Cl | H | $C_2H_5$ | O | 4-$NO_2$, H | " | ($CDCl_3$) 1.16(3H, t, J=6.6), 2.14(2H, m), 4.47(1H, t, J=6.0), 6.67–8.09(16H, m) | 40 |
| 1-10 | CH | CH | Cl | H | n-$C_3H_7$ | O | 4-$NO_2$, H | " | ($CDCl_3$) 1.05(3H, t, J=6.6), 1.30–2.34 (4H, m), 4.81(1H, t, J=6.6), 6.57–8.16 (16H, m) | 20 |
| 1-11 | CH | CH | $NO_2$ | H | $CH_3$ | O | 4-$NO_2$, H | " | ($CDCl_3$) 1.84(3H, d, J=6.6), 5.04(1H, q, J=6.6), 6.70–8.20(16H, m) | 80 |
| 1-12 | CH | CH | H | H | $CH_3$ | O | 4-$NO_2$, H | Oily substance | ($CDCl_3$) 1.77(3H, d, J=7.2), 4.93(1H, q, J=7.2), 6.79–8.17(17H, m) | 56 |
| 1-13 | N | CH | $CF_3$ | Cl | $CH_3$ | O | 4-$NO_2$, H | " | ($CDCl_3$) 1.81(3H, d, J=6.6), 4.97(1H, q, J=6.6), 6.88–8.21(14H, m) | 97 |
| 1-14 | N | CH | $CF_3$ | Cl | $CH_3$ | O | 2-$NO_2$, H | " | ($CDCl_3$) 1.78(3H, d, J=7.2), 4.96(1H, q, J=7.2), 6.86–8.20(14H, m) | 86 |
| 1-15 | N | CH | $CF_3$ | Cl | $CH_3$ | O | 4-$NO_2$, 3-Cl | " | ($CDCl_3$) 1.79(3H, d, J=6.6), 4.96(1H, q, J=6.6), 6.74–8.20(13H, m) | 66 |
| 1-16 | N | CH | $CF_3$ | Cl | $CH_3$ | O | 4-$NO_2$, 2-Cl | " | ($CDCl_3$) 1.82(3H, d, J=7.0), 5.02(1H, q, J=7.0), 6.86–8.36(13H, m) | 68 |
| 1-17 | N | N | $CF_3$ | Cl | $CH_3$ | O | 3-Cl, 5-$CF_3$ | " | ($CDCl_3$) 1.90(3H, d, J=7.0), 5.09(1H, q, J=7.0), 7.17–8.36(12H, m) | 72 |
| 1-18 | N | CH | $CF_3$ | Cl | $CH_3$ | N | 4-$NO_2$, H | Oily substance | ($CDCl_3$) 1.70(3H, d, J=6.6), 4.79(1H, q, J=6.6), 6.87–8.24(14H, m), 8.36(1H, s) | 98 |
| 1-19 | N | N | $CF_3$ | Cl | $CH_3$ | N | 3-Cl, 5-$CF_3$ | " | ($CDCl_3$) 1.72(3H, d, J=7.0), 4.82(1H, q, J=7.0), 7.08–8.30(13H, m) | 75 |
| 1-20 | N | CH | $CF_3$ | H | $CH_3$ | O | 4-$NO_2$, H | " | ($CDCl_3$) 1.79(3H, d, J=6.6), 4.95(1H, q, J=6.6), 6.82–7.34(15H, m) | 40 |
| 1-21 | N | CH | $CF_3$ | H | $CH_3$ | O | 2-$NO_2$, H | " | ($CDCl_3$) 1.79(3H, d, J=6.6), 4.97(1H, q, J=6.6), 6.86–8.37(15H, m) | 89 |
| 1-22 | N | CH | $CF_3$ | H | $CH_3$ | O | 4-$NO_2$, 3-Cl | " | ($CDCl_3$) 1.80(3H, d, J=6.6), 4.96(1H, q, J=6.6), 6.86–8.36(14H, m) | 93 |
| 1-23 | N | CH | $CF_3$ | H | $CH_3$ | O | 4-$NO_2$, 2-Cl | " | ($CDCl_3$) 1.82(3H, d, J=7.0), 5.02(1H, q, J=7.0), 6.84–8.41(14H, m) | 74 |

REFERENCE EXAMPLE 3: SYNTHESIS OF STARTING MATERIAL HAVING THE FORMULA (3-2)

(A) 4-Aminobenzenesulfonamide

To 4-nitrobenzenesulfonyl chloride (6.7 g) was added ammonia water (10 ml) while ice-cooling, and the mixture was stirred at room temperature for 3 hours. The reaction mixture was extracted with ethyl acetate (100 ml), and the extract was washed with water and saturated aqueous sodium chloride and dried over anhydrous sodium sulfate, followed by evaporation of the solvent under a reduced pressure, to obtain 4-nitrobenzenesulfonamide (5.9 g).

The 4-nitrobenzenesulfonamide obtained (5.9 g) was dissolved in methanol (100 ml), and after an addition of conc. hydrochloric acid, reduced iron (4.2 g) was added and the mixture stirred at room temperature for 2 hours. After filtration, methanol was evaporated under a reduced pressure, the residue was made basic with an addition of 4N sodium hydroxide, and the mixture of the desired product and iron oxide precipitated was collected by filtration. The mixture was dissolved in acetone (200 ml), filtered to remove iron oxide, and the solvent was evaporated under a reduced pressure to obtain 4-aminobenzenesulfonamide (3.7 g) (m.p. 164° C.–165.5° C.).

By using (a) 2-nitrobenzenesulfonyl chloride, (b) 3-nitrobenzenesulfonyl chloride instead of 4-nitrobenzenesulfonyl chloride in the above (A), (a') 2-aminobenzenesulfonamide (m.p. 184° C.–186° C.), (b') 3-aminobenzenesulfonamide (m.p. 139° C. –140° C.) were obtained respectively.

(B) N-methyl-4-(amino)benzenesulfonamide

To a solution of methylamine hydrochloride (1.4 g) in pyridine (5 ml) was added 4-acetamidobenzenesulfonyl chloride (2.3 g), and the mixture was stirred at 50° C. for 2 hours. The residue obtained by an evaporation of pyridine under a reduced pressure was dissolved in methylene chloride (50 ml), washed with water, 1N hydrochloric acid, and saturated aqueous sodium chloride, and dried over anhydrous sodium sulfate. Evaporation of the solvent under a reduced pressure gave N-methyl-4-(acetamido)benzenesulfonamide (1.6 g).

The acetamide (1.6 g) was dissolved in methanol (5 ml) and refluxed, with an addition of 4N hydrochloric acid (7 ml), for 1 hour. After an evaporation of methanol under a reduced pressure, the residue was made basic with an addition of 1N sodium hydroxide, and extracted with ethyl acetate (30 ml), followed by drying over anhydrous sodium sulfate. Evaporation of the solvent under a reduced pressure gave N-methyl-4-(amino)benzenesulfonamide (1.2 g) (m.p. 110.9° C.–112° C.).

In the above (B), instead of methylamine hydrochloride, (a) O,N-dimethylhydroxylamine hydrochloride, (b) diethylamine were employed to obtain (a') N-methyl-N-methoxy-4-(amino)benzenesulfonamide (m.p. 119° C.–120° C.), (b') N,N-diethyl-4-(amino)benzenesulfonamide (m.p. 102° C.–103.5° C.), respectively.

(C) N,N,Diethyl-3-(amino)benzenesulfonamide

Diethylamine (2.4 g) was dissolved in pyridine (15 ml) and 3-nitrobenzenesulfonyl chloride (6.7 g) was added, followed by stirring at 50° C. for 2 hours. The residue obtained by an evaporation of pyridine under a reduced pressure was dissolved in methylene chloride (150 ml), washed with water, 1N hydrochloric acid, water, and saturated aqueous sodium chloride, and dried over anhydrous sodium sulfate. Evaporation of the solvent under a reduced pressure gave N,N-diethyl-3-(nitro)benzenesulfonamide (4.0 g).

The N,N-diethyl-3-(nitro)benzenesulfonamide (3.9 g) was dissolved in methanol (60 ml) and, after an addition of conc. hydrochloric acid (10 ml), reduced iron (4.2 g) was added and the mixture was stirred at room temperature for 2 hours. After filtration, methanol was evaporated under a reduced pressure and the residue was made basic with an addition of 4N sodium hydroxide. The iron oxide precipitated was separated by filtration, washed with methylene chloride (50 ml). Also the filtrate was extracted with methylene (50 ml×2) and combined with the methylene chloride washing, followed by drying over anhydrous sodium sulfate. Evaporation of the solvent gave N,N-diethyl-3-(amino)benzenesulfonamide (3.0 g) (m.p. 82°–84° C.).

EXAMPLE 2-1

4-(2-(4-(3-Chloro-5-trifluoromethyl-2-pyridyloxy)-phenoxy)propanamido)benzenesulfonamide (2-(4-(3-Chloro-5-trifluoromethyl-2-pyridyloxy)-phenoxy)propionic acid chloride hydrochloride (0.8 g) and 4-aminobenzene sulfonamide (0.5 g) were dissolved in dry tetrahydrofuran (20 ml), and the solution was stirred, with an addition of triethylamine (0.6 ml) at room temperature for 2 hours. After completion of the reaction, the solvent was evaporated under a reduced pressure, the residue was dissolved in methylene chloride and washed with 1N hydrochloric acid, water, saturated aqueous sodium hydrogen carbonate, water and saturated aqueous sodium chloride. After drying over anhydrous sodium sulfate, the residue obtained by evaporation of the solvent under a reduced pressure was purified by medium pressure column chromatography by using silica gel, to obtain the title compound (0.8 g).

EXAMPLE 2-2

3-(2-(4-(3-Chloro-5-trifluoromethyl-2-pyridyloxy)-phenoxy)propanamido)benzenesulfonamide In Example 2-1, by using 3-aminobenzene sulfonamide instead of 4-aminobenzenesulfonamide, the title compound was obtained.

EXAMPLE 2-3

2-(2-(4-(3-Chloro-5-trifluoromethyl-2-pyridyloxy)-phenoxy)propanamide)benzenesulfonamide In Example 2-1, by using 2-aminobenzenesulfonamide instead of 4-aminobenzenesulfonamide, the title compound was obtained.

EXAMPLE 2-4

N-Methyl-4-(2-(4-(3-chloro-5-trifluoromethyl-2-pyridyloxy)phenoxy)propanamido)benzenesulfonamide In Example 2-1, by using N-methyl-4-(amino)benzenesulfonamide instead of 4-aminobenzenesulfonamide, the title compound was obtained.

EXAMPLE 2-6

N-Methyl-N-methoxy-5-trifluoromethyl-2-pyridyloxy)-phenoxy)propanamido)benzenesulfonamide In Example 2-1, by using N-methyl-N-methoxy-4-(amino)benzenesulfonamide instead of 4-aminobenzenesulfonamide, the title compound was obtained.

EXAMPLE 2-7

N-(Methoxycarbonyl)4-(2-(4-(3-chloro-5-trifluoromethyl-2-pyridyloxy)phenoxy)propanamide)benzenesulfonamide In Example 2-1, by using N-(methoxycarbonyl)-4-(amino)benzenesulfonamide instead of 4-aminobenzenesulfonamide, the title compound was obtained.

EXAMPLE 2-8

N,N-diethyl-3-(2-(4-(3-chloro-5-trifluoromethyl-2-pyridyloxy)phenoxy)propanamide)benzenesulfonamide In Example 2-1, by using N,N-diethyl-3-4(amino)benzenesulfonamide instead of 4-aminobenzenesulfonamide, the title compound was obtained.

EXAMPLE 2-9

4-(4-(3-Chloro-5-trifluoromethyl-2-pyridyloxy)phenoxyacetamide)benzenesulfonamide In Example 2-1, by using 4-(3-chloro-5-trifluoromethyl-2-pyridyloxy)phenoxyacetic acid chloride hydrochloride instead of 2-(4-(3-chloro- 5-trifluoromethyl-2-pyridyloxy)phenoxy)propionic acid chloride hydrochloride, the title compound was obtained.

EXAMPLE 2-10

4-(2-(4-(5-Trifluoromethyl-2-pyridyloxy)phenoxy)-propanamide)benzenesulfonamide

In Example 2-1, by using 2-(4-(5-trifluoromethyl-2-pyridyloxy)phenoxypropionic acid chloride hydrochloride instead of 2-(4-(3-chloro-5-trifluoromethyl-2-pyridyloxy)phenoxy)propionic acid chloride hydrochloride, the title compound was obtained.

EXAMPLE 2-11

4-(2-(4-(4-Chlorophenoxy)phenoxy)propanamido)benzenesulfonamide

In Example 2-1, by using 2-(4-(4-chlorophenoxy)-phenoxy)propionic acid chloride hydrochloride instead of 2-(4-(3-chloro-5-trifluoromethyl-2-pyridyloxy)-phenoxy)propionic acid chloride, the title compound was obtained.

The physicochemical data of the compounds obtained is shown in Table 2.

TABLE 2

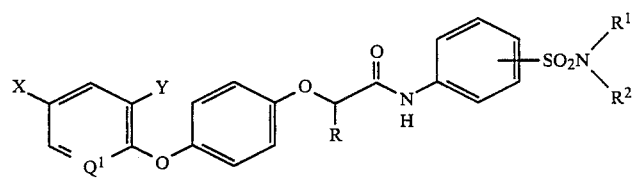

| Example No. | $Q^1$ | X | Y | R | $NR^1R^2$ | Property | NMR Spectrum/δ ppm (J/Hz) | Yield (%) |
|---|---|---|---|---|---|---|---|---|
| 2-1 | N | $CF_3$ | Cl | $CH_3$ | 4,$NH_2$ | mp 195–97° C. | ($CD_3OD$)1.66(3H, d, J=6.6), 4.86 (1H, q, J=6.6), 7.08–8.23(10H, m) | 78 |
| 2-2 | N | $CF_3$ | Cl | $CH_3$ | 3,$NH_2$ | Oily substance | ($CDCl_3$)1.63(3H,d,J=7.0), 4.76(1H, q, J=7.0), 5.38(2H, s), 6.93–8.22(10H, m), 8.58(1H, s) | 53 |
| 2-3 | N | $CF_3$ | Cl | $CH_3$ | 2,$NH_2$ | Oily substance | ($CDCl_3$)1.70(3H, d, J=7.0), 4.78(1H, q, J=7.0), 4.91(2H, s), 6.98–8.42(10H, m), 10.12(1H, s) | 61 |
| 2-4 | N | $CF_3$ | Cl | $CH_3$ | 4,$NHCH_3$ | Oily substance | ($CDCl_3$)1.62(3H, d, J=6.0), 2.56(3H, d, J=5.4), 4.65(1H, q, J=5.4), 4.74(1H, q, J=6.0), 6.98–8.17(10H, m), 8.42(1H, s) | 98 |
| 2-5 | N | $CF_3$ | Cl | $CH_3$ | 4,N($CH_3$)($OCH_3$) | Oily substance | ($CDCl_3$)1.58(3H, d, J=6.0), 2.60(3H, s), 3.61(3H, s), 4.61(1H, q, J=6.0), 6.70–8.04(10H, m), 8.37(1H, s) | 99 |
| 2-6 | N | $CF_3$ | Cl | $CH_3$ | 4,N($C_2H_5$)$_2$ | Oily substance | ($CDCl_3$)1.10(6H, t, J=7.0), 1.64(3H, d, J=7.0), 3.18(4H, q, J=7.0), 4.76(1H, q, J=7.0), 6.94–8.22(10H, m), 8.42(1H, s) | 94 |
| 2-7 | N | $CF_3$ | Cl | $CH_3$ | 4,$NHCO_2CH_3$ | mp 214–216° C. | ($CD_3OD$)1.63(3H, d, J=7.2), 3.60(3H, s), 4.74(1H, q, J=7.2), 7.03–8.20(10H, m) | 96 |
| 2-8 | N | $CF_3$ | Cl | $CH_3$ | 3,N($C_2H_5$)$_2$ | Oily substance | ($CDCl_3$)1.16(6H, 5, J=7.0), 1.69(3H, d, J=7.0), 3.27(4H, q, J=7.0), 4.81(1H, q, J=7.0), 6.97–8.26(10H, m), 8.54(1H, s) | 92 |
| 2-9 | N | $CF_3$ | Cl | H | 4,$NH_2$ | mp 205–206.5° C. | (Acetone-$d_6$)4.76(2H, s), 6.49(2H, s), 7.05–8.37(10H, m) | 55 |
| 2-10 | N | $CF_3$ | H | $CH_3$ | 4,$NH_2$ | mp 173.5–175° C. | (Acetone-$d_6$)1.62(3H, d, J=7.0), 4.91(1H, q, J=7.0), 6.51(2H, s), 7.12–8.44(11H, m), 9,67(1H, s) | 65 |
| 2-11 | CH | Cl | H | $CH_3$ | 4,$NH_2$ | mp 198–199.5° C. | (Acetone-$d_6$)1.61(3H, d, J=7.0), 4.87(1H, q, J=7.0), 6.47(2H, s), 6.88–7.95(12H, m), 9.62(1H, s) | 50 |

EXAMPLE 3-1

(3-Bromo-2-oxo)propyl 2-[4-(3-chloro-5-trifluoromethyl-2-pyridyloxy)phenoxy]propionate 2-[4-(3-Chloro-5-trifluoromethyl-2-pyridyloxy)phenoxy]propionic acid (1.6 g) was dissolved in 10 ml of dimethylformamide, and the solution was stirred with an addition of 1 ml of dicyclohexylamine at 40° C. Then, 710 mg of 3-chlorodiazoacetone was added dropwise, and the mixture was further stirred for 2 hours. The reaction mixture was washed with water, extracted with ether, and the extract was dried over anhydrous magnesium sulfate. The oily product obtained by evaporation of ether under a reduced pressure was subjected to silica gel medium pressure column chromatography (n-hexane/ethyl acetate), to obtain 1.32 g of a diazomethylketone derivative as a colorless oily product.

The compound (300 mg) as prepared above was dissolved in 10 ml of ether, and 230 mg of 47% hydrobromic acid was added, followed by stirring for 30 minutes. The reaction mixture was washed with water, dried over anhydrous magnesium sulfate, and ether was evaporated under a reduced pressure to give 270 mg of the title compound as a colorless oily product.

EXAMPLE 3-2

(3,3-Dibromo-2-oxo)propyl 2[4-(3-chloro-5-trifluoromethyl-2-pyridyloxy)phenoxy]propionate The synthetic intermediate (3-diazo-12-oxopropyl) 2[4-(3-chloro-5-trifluoromethyl-2-pyridyloxy)phenoxy]propionate (300 mg) was dissolved in 40 ml of carbon tetrachloride, and a solution of 22 mg of bromine in 5 ml of carbon tetrachloride was added at 0° C. After stirring for 30 minutes, the solvent was evaporated under a reduced pressure, and the residue was subjected to silica gel medium pressure column chromatography (n-hexane/ethyl acetate), to obtain 200 mg of the title compound as a colorless oily product.

EXAMPLE 3-3

(3-Chloro-2-oxo)propyl 4-(3-chloro-5-trifluoromethyl-2-pyridyloxy)phenoxyacetate 4-(3-Chloro-5-trifluoromethyl-2-pyridyloxy)phenoxyacetic acid (1.7 g) was dissolved in 30 ml of dimethylformamide, the solution was stirred with an addition of 1 ml of dicyclohexylamine at 60° C., added into 30 ml of a solution of 1.9 g of 1,3-dichloroacetone in dimethylformamide, and the mixture was further stirred for 2 hours. After the reaction, the product was washed with water, extracted with ethyl acetate, and the extract washed with 1N hydrochloric acid, followed by drying over anhydrous magnesium sulfate. The oily product obtained by evaporation of the solvent under a reduced pressure was subjected to silica gel medium pressure column chromatography (n-hexane/ethyl acetate), to obtain 1.45 g of the title compound as a colorless oily product.

EXAMPLE 3-4

N-[2-{4-(3-chloro-5-trifluoromethyl-2-pyridyloxy)phenoxy}propionyl]alanine chloromethyl ketone N-[2-{4-(3-chloro-5-trifluoromethyl-2-pyridyloxy)phenoxy}propionylalanine (400 mg) was dissolved in 10 ml of tetrahydrofuran, added with 0.15 ml of triethylamine and cooled to 0° C. Ethyl chlorocarbonate (0.1 ml) was added and after 5 minutes, excessive diazomethane ether solution was added, and the mixture was stirred for one hour. Then, several drops of conc. hydrochloric acid were added and, after stirring for 10 minutes, the reaction mixture was washed with water, extracted with ether, and the extract dried over anhydrous magnesium sulfate. The oily product obtained by evaporation of the solvent under a reduced pressure was subjected to silica gel medium pressure column chromatography to obtain 300 mg of the title compound as a colorless oily product.

EXAMPLE 3-5

(3-Chloro-2oxo-1,1-dimethyl)propyl 2-[4-(3-chloro-5-trifluoromethyl-2-pyridyloxy)phenoxy]propionate 2-[2-{4-(3-Chloro-5-trifluoromethyl-2-pyridyloxy)phenoxy}propionyloxy]isobutyric acid (3.1 g) was dissolved in 50 ml of benzene, 2 ml of thionyl chloride was added to the solution, and the mixture was stirred under heating at 90° C. for one hour. Benzene was evaporated under a reduced pressure, a small amount of ether was added and excessive diazomethane ether solution was added while cooling. After stirring for one hour, while hydrogen chloride gas was passed therethrough, the mixture was stirred at room temperature for 30 minutes. The reaction mixture was washed with water, dried over anhydrous magnesium sulfate and the solvent was evaporated under a reduced pressure. The oily product obtained was subjected to silica gel medium pressure column chromatography (n-hexane/ethyl acetate) to obtain 3.4 g of the title product as a colorless oily product.

According to the same method as described above in Examples 3-1 to 3-5, the compounds of Example Nos. 3-6 to 3-9 were synthesized by using preparation method A, the compounds of Example Nos. 3-10 to 3-15 by using preparation method B and the compounds of Example Nos. 3-16 to 3-18, respectively.

The physical property values of the compounds synthesized above are shown in Table 3.

TABLE 3

| Example No. | Y | $X^1$ | R | $R^3$ | $R^4$ | $R^5$ | $R^6$ | Z | $Q^1$ | Property |
|---|---|---|---|---|---|---|---|---|---|---|
| 3-1 | Cl | Br | Me | H | H | H | H | O | N | $n_D^{25}$ 1.4960 |
| 3-2 | Cl | Br | Me | H | H | H | Br | O | N | $n_D^{25}$ 1.5123 |
| 3-3 | Cl | Cl | H | H | H | H | H | O | N | m.p. 118° C. |

TABLE 3-continued $$CF_3\text{-pyridyl(Q}^1\text{)}-Y-\text{C}_6\text{H}_4-O-CH(R)-C(=O)-Z-CR^3R^4-CO-CR^5R^6-X^1$$

| Example No. | Y | X¹ | R | R³ | R⁴ | R⁵ | R⁶ | Z | Q¹ | Property |
|---|---|---|---|---|---|---|---|---|---|---|
| 3-4 | Cl | Cl | Me | Me | H | H | H | NH | N | m.p. 119° C. |
| 3-5 | Cl | Cl | Me | Me | Me | H | H | O | N | m.p. 76° C. |
| 3-6 | Cl | Br | Me | H | H | H | H | O | CH | $n_D^{25}$ 1.5367 |
| 3-7 | Cl | Cl | Me | Me | H | H | H | O | N | $n_D^{25}$ 1.5220 |
| 3-8 | Cl | I | Me | H | H | H | H | O | N | $n_D^{25}$ 1.5233 |
| 3-9 | Cl | Br | Me | Me | H | H | H | O | N | $n_D^{25}$ 1.5236 |
| 3-10 | Cl | Cl | Me | H | H | H | H | O | CH | $n_D^{25}$ 1.5068 |
| 3-11 | Cl | Cl | Me | H | H | H | H | O | N | $n_D^{25}$ 1.5287 |
| 3-12 | H | Cl | Me | H | H | H | H | O | N | $n_D^{25}$ 1.5225 |
| 3-13 | Cl | Br | Me | H | H | Me | Me | O | N | $n_D^{25}$ 1.5222 |
| 3-14 | Cl | Cl | Me | H | H | Me | H | O | N | $n_D^{25}$ 1.5184 |
| 3-15 | Cl | F | Me | H | H | H | H | O | N | $n_D^{25}$ 1.5089 |
| 3-16 | Cl | Cl | H | Me | Me | H | H | NH | N | m.p. 83° C. |
| 3-17 | Cl | Cl | Me | Me | Me | H | H | NH | N | m.p. 81° C. |
| 3-18 | H | Cl | H | Me | Me | H | H | O | N | m.p. 111° C. |

$n_D^{25}$ = Index of Refraction, m.p. = melting point, Me = CH₃

EXAMPLE 4-1

{3-(4-Chlorophenoxy)-2-oxo)propyl 2-{4-(3-chloro-5-trifluoromethyl-2-pyridyloxy)phenoxy}propionate 2-{4-(3-Chloro-5-trifluoromethyl-2-pyridyloxy)-phenoxy}propionic acid (724 mg) was dissolved in 20 ml of dimethylformamide, 0.4 ml of dicyclohexylamine was added to the solution and the mixture was stirred at 50° C. Then, 420 mg of 1-chloro-3-(4-chlorophenoxy-)acetone was added, and further stirring was continued at 50° C. for 3 hours. To the reaction mixture was added 30 ml of water, the mixture was extracted with ethyl acetate and the extract washed with water, followed by drying over anhydrous magnesium sulfate. The oily product obtained by evaporation of the solvent under a reduced pressure was subjected to silica gel medium pressure column chromatography [(n-hexane:ethyl acetate=6:1 (v/v)], to obtain 600 mg of the title compound as a colorless oily product.

EXAMPLE 4-2

(3-Acetoxy-2-oxo-)propyl 2-{4-(3-chloro-5-trifluoromethyl-2-pyridyloxy)phenoxy}propionate 2-{4-(3-Chloro-5-trifluoromethyl-2-pyridyloxy)-phenoxy}propionic acid (1.81 g) was dissolved in 100 ml of dimethylformamide, 1 ml of dicyclohexylamine was added and the mixture was stirred at 50° C. Then, 1.9 g of 1,3-dichloroacetone was added, and the mixture was further stirred at 50° C. for 3 hours. To the reaction mixture was added 100 ml of water, the mixture extracted with ethyl acetate, and the extract washed with water, followed by drying over anhydrous magnesium sulfate. The oily product obtained by evaporation of the solvent under a reduced pressure was subjected to silica gel medium pressure column chromatography [(n-hexane:ethyl acetate=9:1 (v/v)], to obtain 1.43 g of a chloromethyl ketone derivative as a colorless oily product.

To a solution of 0.6 ml of acetic acid in 10 ml of dimethylformamide was added 0.2 ml of dicyclohexylamine, and the mixture was stirred at 50° C. Then, 452 mg of the above chloromethyl ketone derivative was added, and further, the mixture was stirred at 50° C. for 3 hours. To the reaction mixture was added 10 ml of water, the mixture was extracted with ethyl acetate, and the extract washed with water, followed by drying over anhydrous magnesium sulfate. The oily product obtained by evaporation of the solvent under a reduced pressure was subjected to silica gel medium pressure column chromatography [(n-hexane:ethyl acetate=9:1 (v/v)], to obtain 310 mg of the title compound as a colorless oily product.

Also, according to the same method as in the above Example 4-1, the following compounds of Example 4-2, 4-4, 4-8, 4-9, 4-10, 4-11, 4-12, 4-13, 4-14 and 4-15 were synthesized by using the preparation process A, and according to the same method as in the above Preparation example 4-2, the following compounds of Examples 4-5, 4-6 and 4-7 were synthesized by using the preparation process B.

The structures and the physical property values of the compounds synthesized above are shown in Table 4.

TABLE 4

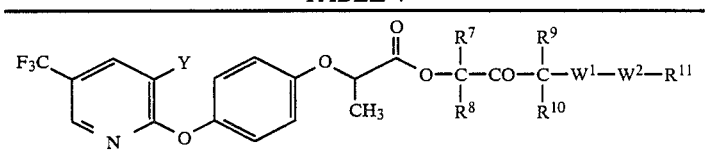

| Example No. | Y | R⁷ | R⁸ | R⁹ | R¹⁰ | W¹ | W² R¹¹ | Property |
|---|---|---|---|---|---|---|---|---|
| 4-1 | Cl | H | H | H | H | O | 4-chlorophenyl | $n_D^{25}$ 1.4984 |
| 4-2 | Cl | H | H | H | H | O | CH₃ | $n_D^{25}$ 1.5041 |

TABLE 4-continued

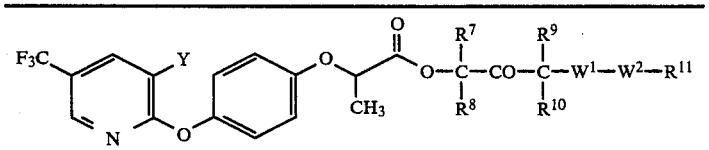

| Example No. | Y | R⁷ | R⁸ | R⁹ | R¹⁰ | W¹ | W²R¹¹ | Property |
|---|---|---|---|---|---|---|---|---|
| 4-3 | Cl | H | H | H | H | O | COCH₃ | $n_D^{25}$ 1.4858 |
| 4-4 | Cl | H | H | H | H | O | 4-chlorophenoxyl | $n_D^{25}$ 1.5349 |
| 4-5 | Cl | H | H | H | H | O | 4-benzoyl | mp 103° C. |
| 4-6 | Cl | H | H | H | H | O | 3-phenylpropionyl | $n_D^{25}$ 1.5208 |
| 4-7 | Cl | H | H | H | H | O | COCH=CH₂ | $n_D^{25}$ 1.4996 |
| 4-8 | Cl | H | H | H | H | O | H | $n_D^{25}$ 1.4930 |
| 4-9 | Cl | Me | H | H | H | O | H | $n_D^{25}$ 1.4812 |
| 4-10 | Cl | Me | Me | H | H | O | H | $n_D^{25}$ 1.5130 |
| 4-11 | Cl | H | H | Me | Me | O | H | $n_D^{25}$ 1.5024 |
| 4-12 | H | H | H | H | H | O | H | $n_D^{25}$ 1.4916 |
| 4-13 | Cl | H | H | H | H | N | COO(t-Bu) | $n_D^{25}$ 1.5074 |
| 4-14 | Cl | H | H | Me | H | N | COCH₃ | $n_D^{25}$ 1.5180 |
| 4-15 | Cl | H | H | Me | H | N | COCF₃ | $n_D^{25}$ 1.4989 |

EXAMPLE 5-1

2-(4-(3-Chloro-5-trifluoromethyl-2-pyridyloxy)phenoxy)propionic acid 5-(2,4-dichlorophenoxy)-2-nitrophenyl ester:

5-(2,4-Dichlorophenoxy)-2-nitrophenol (0.8 g) and triethylamine (0.6 ml) were dissolved in dry tetrahydrofuran (10 ml), and the solution was stirred at room temperature for 2 hours, with an addition of a solution of 2-(4-(3-chloro-5-trifluoromethyl-2-pyridyloxy)phenoxy)propionic acid chloride (0.8 g), in dry tetrahydrofuran (10 ml). After completing the reaction, the solvent was distilled off under a reduced pressure and the residue was dissolved in methylene chloride (20 ml), followed by washing with 1N hydrochloric acid, water, a saturated aqueous sodium bicarbonate solution, water, and a saturated aqueous sodium chloride solution. The resultant reaction mixture was dried over anhydrous magnesium sulfate, ether was evaporated under a reduced pressure, and the resultant residue was subjected to silica gel medium pressure column chromatography for purification. Thus, the title compound (0.9 g) was obtained in the form of a colorless oily product.

The compounds of Examples 4-2 to 4-7 were synthesized in same manner as in Example 4-1.

The physical property data of the resultant compounds is shown in Table 5.

EXAMPLE 6-1

2-(4(3-Chloro-5-trifluoromethyl-2-pyridyloxy)phenoxy)propionic acid 2-oxopropyl ester:

2-(4-(3-Chloro-5-trifluoromethyl-2-pyridyl-oxy)-phenoxy) propionic acid (3.62 g) was dissolved in dimethylformamide (50 ml) and the solution was stirred with an addition of dicyclohexylamine (2.2 ml). The mixture was further stirred at a temperature of 60° C. for 3 hours. To the reaction mixture, 100 ml of water was added, followed by extracting with toluene. After washing with water, the mixture was dried over anhydrous magnesium sulfate, the solvent was distilled off under a reduced pressure, and the resultant oily product was subjected to silica gel medium pressure column chromatography (n-hexane/ethyl acetate=9/1 v/v%) to obtain 4.00 g of the title compound in the form of a colorless oily product (yield=96%).

The compounds of Examples 6-2 to 6-11 were synthesized in the same manner as in Example 6-1.

The structures and the physical properties of the compounds are shown in Table 6.

TABLE 5

| Example No. | Q¹ | Q³ | Z | V³ | R | Property |
|---|---|---|---|---|---|---|
| 5-1 | N | CH | O | Cl | CH₃ | $n_D^{25}$ 1.5163 |
| 5-2 | N | N | O | CF₃ | CH₃ | mp 72–74° C. |
| 5-3 | N | CH | O | CF₃ | CH₃ | $n_D^{25}$ 1.5210 |
| 5-4 | CH | CH | O | CF₃ | CH₃ | $n_D^{25}$ 1.5047 |
| 5-5 | N | CH | O | CF₃ | H | $n_D^{25}$ 1.5024 |
| 5-6 | CH | CH | O | CF₃ | H | $n_D^{25}$ 1.5030 |
| 5-7 | N | CH | NH | CF₃ | CF₃ | mp 136–137° C. |

TABLE 6

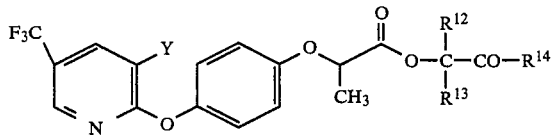

| Example No. | Y | $R^{12}$ | $R^{13}$ | $R^{14}$ | Property |
|---|---|---|---|---|---|
| 6-1 | Cl | H | H | CH$_3$ | $n_D^{25}$ 1.5069 |
| 6-2 | Cl | H | H | C$_2$H$_5$ | $n_D^{25}$ 1.5012 |
| 6-3 | Cl | H | H | C$_6$H$_5$ | $n_D^{25}$ 1.4960 |
| 6-4 | Cl | H | —CH$_2$—CH$_2$—CH$_2$— | | $n_D^{25}$ 1.5132 |
| 6-5 | Cl | CH$_3$ | H | CH$_3$ | $n_D^{25}$ 1.5086 |
| 6-6 | Cl | H | H | t-butyl | $n_D^{25}$ 1.4962 |
| 6-7 | Cl | H | H | 2,5-dimethoxyphenyl | mp 65° C. |
| 6-8 | Cl | H | H | 4-fluorophenyl | mp 96° C. |
| 6-9 | Cl | H | H | 3,4-dihydroxyphenyl | $n_D^{25}$ 1.4903 |
| 6-10 | Cl | H | H | 4-nitrophenyl | mp 125° C. |
| 6-11 | H | H | H | CH$_3$ | $n_D^{25}$ 1.4984 |

FORMULATION EXAMPLE 1 (EMULSION)

In the present compound (Compound in Example 3-11), as the active ingredient, (15 parts by weight), 65 parts by weight of xylene, and 20 parts by weight of a polyoxyethylene alkyl allyl ether were mixed into a homogeneous solution to obtain an emulsion containing 15% of the active ingredient. During usage, the emulsion was diluted with water to a predetermined concentration before spraying.

FORMULATION EXAMPLE 2 (WETTABLE AGENT)

In the present compound (Compound in Example 4-8), as the active ingredient, (40 parts by weight), 55 parts by weight of Zieglight, 2 parts by weight of sodium alkylbenzenesulfonate and 3 parts by weight of a poloxyethylene alkyl aryl ether were mixed and pulverized to obtain a wettable agent containing 40% of the active ingredient compound. During usage, the agent was diluted with water to a predetermined concentration before spraying.

FORMULATION EXAMPLE 3 (GRANULE)

In the present compound (Compound in Example 6-1), as the active ingredient, (5 parts by weight), 20 parts by weight of bentonite, 73 parts by weight of clay, and 2 parts by weight of sodium dodecylbenzenesulfonate were mixed and kneaded with an addition of about 20 parts by weight of water by a kneader. The kneaded product was granulated through a granulator, and subsequently dried and classified into regular sizes to prepare granules containing 5% of the active ingredient.

TEST EXAMPLE 1: HERBICIDAL ACTIVITY IN UPLAND CONDITIONS (1) Pre-emergence Test A square pot 7.1×7.1 cm was filled with field soil, and after seeding of Echinochloa crus-galli, Digitaria ciliaris, covered with 5 mm of soil. A predetermined amount of the test compound was diluted with water and 10 liters/are of the dilution was used for treatment of the soil. After the treatment, management was performed in a greenhouse for 20 days, and the herbicidal effect was evaluated by observation according to following standards, to obtain the results shown in Table 7.

| Mark | Degree of the damage |
|---|---|
| 5: | complete death |
| 4: | severe |
| 3: | moderate |
| 2: | mild |
| 1: | slight |
| 0: | none |

TABLE 7

| Example No. | Application rate (g/a) | Echinochloa crus-galli | Digitaria ciliaris | Polygonum lapathifolium | Amaranthus viridis |
|---|---|---|---|---|---|
| 1-2 | 40 | 5 | 4 | — | — |
| 1-6 | 40 | 5 | 4 | — | — |
| 1-13 | 40 | 5 | 5 | — | — |
| 1-15 | 40 | 5 | 5 | — | — |
| 1-22 | 40 | 5 | 5 | — | — |
| 2-1 | 40 | 5 | 5 | — | — |
| 2-2 | 40 | 5 | 5 | — | — |
| 2-7 | 40 | 5 | 5 | — | — |
| 3-7 | 40 | 5 | 5 | 0 | 0 |
| 3-10 | 20 | 5 | 5 | 0 | 0 |
| 3-14 | 20 | 5 | 5 | 0 | 0 |
| 3-17 | 20 | 5 | 5 | 0 | 0 |
| 4-2 | 40 | 5 | 5 | 0 | 0 |
| 4-3 | 20 | 5 | 5 | 0 | 0 |
| 4-4 | 20 | 5 | 5 | 4 | 4 |
| 4-8 | 20 | 5 | 5 | 0 | 0 |
| 4-9 | 20 | 5 | 5 | 0 | 0 |
| 4-13 | 20 | 5 | 5 | 0 | 0 |
| 5-3 | 20 | 5 | 5 | 4 | 3 |
| 5-4 | 20 | 3 | 4 | 5 | 4 |
| 5-6 | 20 | 2 | 3 | 5 | 5 |
| 6-1 | 20 | 5 | 5 | 0 | 0 |
| 6-4 | 20 | 5 | 5 | 0 | 2 |
| 6-6 | 20 | 5 | 5 | 0 | 0 |
| 6-9 | 20 | 5 | 5 | 0 | 0 |
| 6-11 | 20 | 5 | 5 | 0 | 0 |

(2) Post-emergence Test

A square pot 7.1×7.1 cm was filled with field soil, and after seeding of Echinochloa crus-galli, Digitaria

*ciliaris*, covered with 5 mm of soil. Then, the seeds were allowed to geminate at room temperature for 7 days, and a predetermined amount of the test compound was diluted with water and 10 liters/are of the dilution was used for spraying over the plants. After the treatment, management was performed in a greenhouse for 20 days, and the herbicidal effect was evaluated by observation according to the same standards as in Test Example 1 to obtain the results shown in Table 8.

TABLE 8

| Example No. | Application rate (g/a) | Herbicidal effect | | | |
|---|---|---|---|---|---|
| | | *Echinochloa crus-galli* | *Digitaria ciliaris* | *Polygonum lapathifolium* | *Amaranthus viridis* |
| 1-2 | 40 | 5 | 3 | — | — |
| 1-6 | 40 | 5 | 3 | — | — |
| 1-13 | 40 | 5 | 5 | — | — |
| 1-15 | 40 | 5 | 4 | — | — |
| 1-22 | 40 | 5 | 4 | — | — |
| 2-1 | 40 | 5 | 3 | — | — |
| 2-2 | 40 | 5 | 3 | — | — |
| 2-7 | 40 | 5 | 3 | — | — |
| 3-7 | 40 | 5 | 5 | 5 | 5 |
| 3-9 | 20 | 5 | 5 | 0 | 0 |
| 3-10 | 20 | 5 | 5 | 2 | 4 |
| 3-14 | 20 | 5 | 5 | 0 | 0 |
| 3-17 | 40 | 5 | 5 | 0 | 1 |
| 4-2 | 20 | 5 | 5 | 0 | 0 |
| 4-3 | 20 | 5 | 5 | 0 | 0 |
| 4-4 | 20 | 5 | 5 | 3 | 3 |
| 4-8 | 20 | 5 | 5 | 0 | 0 |
| 4-9 | 20 | 5 | 5 | 0 | 0 |
| 4-13 | 20 | 5 | 5 | 0 | 0 |
| 5-3 | 20 | 5 | 5 | 5 | 5 |
| 5-4 | 20 | 4 | 4 | 5 | 5 |
| 5-6 | 20 | 1 | 2 | 5 | 5 |
| 6-1 | 20 | 5 | 5 | 0 | 0 |
| 6-4 | 20 | 5 | 5 | 2 | 2 |
| 6-6 | 20 | 5 | 5 | 0 | 2 |
| 6-9 | 20 | 5 | 5 | 0 | 0 |
| 6-11 | 20 | 5 | 5 | 2 | 3 |

TEST EXAMPLE 2: HERBICIDAL ACTIVITY IN PADDY CONDITIONS (1) Pre-emergence Test A square pot 7.1×7.1 cm was filled with paddy field soil, submerged to the state of a paddy field, and *Echinochloa oryzicola* and *Monochoria vaginalis* were seeded. Then, a predetermined amount of the test compound in 5 ml/pot of water was applied with a pipette on the water surface. After the treatment, management was performed in a greenhouse for 20 days, and the herbicidal effect was evaluated by observation according to the same standards as in Test Example 1 to obtain the results shown in Table 9.

TABLE 9

| Example No. | Application rate (g/a) | Herbicidal effect | | |
|---|---|---|---|---|
| | | *Echinochloa oryzicola* | *Monochoria vaginalis* | *Cyperus difformis* |
| 1-2 | 40 | 5 | 0 | — |
| 1-6 | 40 | 5 | 0 | — |
| 1-13 | 40 | 5 | 0 | — |
| 1-15 | 40 | 5 | 0 | — |
| 1-22 | 40 | 5 | 0 | — |
| 2-1 | 40 | 5 | 2 | — |
| 2-2 | 40 | 5 | 3 | — |
| 2-7 | 40 | 5 | 5 | — |
| 3-7 | 40 | 5 | 5 | — |
| 3-9 | 20 | 5 | 5 | — |
| 3-10 | 20 | 5 | 5 | — |
| 3-14 | 20 | 5 | 4 | — |
| 3-17 | 40 | 5 | 3 | — |
| 4-2 | 20 | 5 | 1 | — |
| 4-3 | 20 | 5 | 4 | — |
| 4-4 | 20 | 5 | 2 | — |
| 4-8 | 20 | 5 | 3 | — |
| 4-9 | 20 | 5 | 0 | — |
| 4-13 | 20 | 5 | 2 | — |
| 5-3 | 20 | 5 | 5 | 5 |
| 5-6 | 20 | 3 | 5 | 5 |
| 6-1 | 20 | 5 | 3 | — |
| 6-4 | 20 | 5 | 4 | — |
| 6-6 | 20 | 5 | 4 | — |
| 6-9 | 20 | 5 | 2 | — |
| 6-11 | 20 | 5 | 2 | — |

(2) Post-emergence Test

A square pot 7.1×7.1 cm was filled with paddy field soil, submerged to the state of a paddy field, and *Echinochloa oryzicola* and *Monochoria vaginalis* were seeded therein. Then, the seeds were allowed to germinate at room temperature for 7 days, and a predetermined amount of the test compound in 5 ml/pot of water was applied with a pipette on the water surface. After the treatment, management was performed in a greenhouse for 20 days, and the herbicidal effect was evaluated by observation according to the same standards as in Test Example 1 to obtain the results shown in Table 10.

TABLE 10

| Example No. | Application rate (g/a) | Herbicidal effect | | |
|---|---|---|---|---|
| | | *Echinochloa oryzicola* | *Monochoria vaginalis* | *Cyperus difformis* |
| 1-2 | 40 | 5 | 0 | — |
| 1-6 | 40 | 5 | 0 | — |
| 1-13 | 40 | 5 | 0 | — |
| 1-15 | 40 | 5 | 0 | — |
| 1-22 | 40 | 5 | 0 | — |
| 2-1 | 40 | 5 | 0 | — |
| 2-2 | 40 | 5 | 2 | — |
| 2-7 | 40 | 5 | 2 | — |

TABLE 10-continued

| Example No. | Application rate (g/a) | Herbicidal effect |  |  |
|---|---|---|---|---|
| | | Echinochloa oryzicola | Monochoria vaginalis | Cyperus difformis |
| 3-7 | 40 | 5 | 3 | — |
| 3-9 | 20 | 5 | 5 | — |
| 3-10 | 20 | 5 | 5 | — |
| 3-14 | 20 | 5 | 4 | — |
| 3-17 | 40 | 5 | 2 | — |
| 4-2 | 20 | 5 | 0 | — |
| 4-3 | 20 | 5 | 1 | — |
| 4-4 | 20 | 5 | 3 | — |
| 4-8 | 20 | 5 | 3 | — |
| 4-9 | 20 | 5 | 0 | — |
| 4-13 | 20 | 5 | 1 | — |
| 5-3 | 20 | 5 | 3 | 4 |
| 5-4 | 20 | 2 | 3 | 2 |
| 5-6 | 20 | 1 | 5 | 5 |
| 6-1 | 20 | 5 | 3 | — |
| 6-4 | 20 | 5 | 3 | — |
| 6-6 | 20 | 5 | 3 | — |
| 6-9 | 20 | 5 | 2 | — |
| 6-11 | 20 | 5 | 2 | — |

What is claimed is:

1. A compound of the formula:

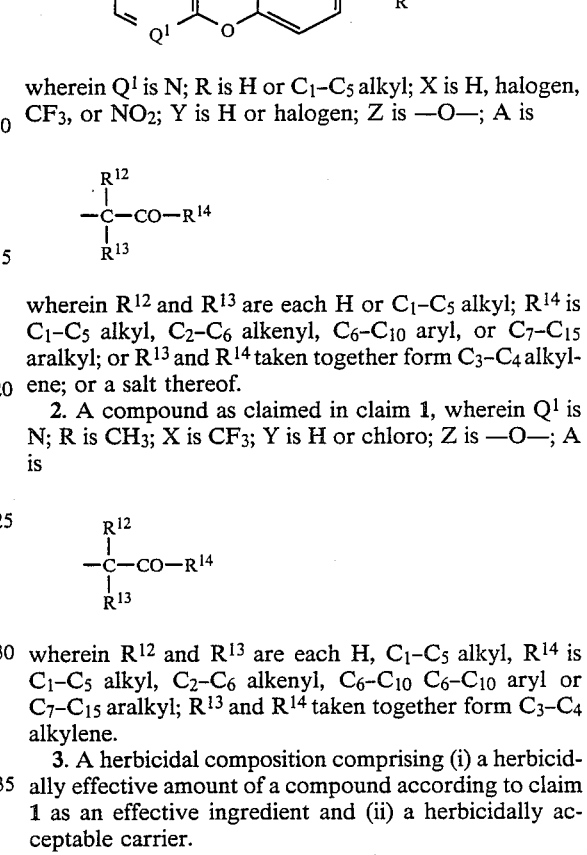

wherein $Q^1$ is N; R is H or $C_1$–$C_5$ alkyl; X is H, halogen, $CF_3$, or $NO_2$; Y is H or halogen; Z is —O—; A is $$-\underset{R^{13}}{\overset{R^{12}}{\underset{|}{\overset{|}{C}}}}-CO-R^{14}$$

wherein $R^{12}$ and $R^{13}$ are each H or $C_1$–$C_5$ alkyl; $R^{14}$ is $C_1$–$C_5$ alkyl, $C_2$–$C_6$ alkenyl, $C_6$–$C_{10}$ aryl, or $C_7$–$C_{15}$ aralkyl; or $R^{13}$ and $R^{14}$ taken together form $C_3$–$C_4$ alkylene; or a salt thereof.

2. A compound as claimed in claim 1, wherein $Q^1$ is N; R is $CH_3$; X is $CF_3$; Y is H or chloro; Z is —O—; A is $$-\underset{R^{13}}{\overset{R^{12}}{\underset{|}{\overset{|}{C}}}}-CO-R^{14}$$

wherein $R^{12}$ and $R^{13}$ are each H, $C_1$–$C_5$ alkyl, $R^{14}$ is $C_1$–$C_5$ alkyl, $C_2$–$C_6$ alkenyl, $C_6$–$C_{10}$ $C_6$–$C_{10}$ aryl or $C_7$–$C_{15}$ aralkyl; $R^{13}$ and $R^{14}$ taken together form $C_3$–$C_4$ alkylene.

3. A herbicidal composition comprising (i) a herbicidally effective amount of a compound according to claim 1 as an effective ingredient and (ii) a herbicidally acceptable carrier.

* * * * *

UNITED STATES PATENT AND TRADEMARK OFFICE
CERTIFICATE OF CORRECTION

PATENT NO. : 4,976,773

DATED : December 11, 1990

INVENTOR(S) : Harukazu FUKAMI et al

It is certified that error appears in the above-identified patent and that said Letters Patent is hereby corrected as shown below:

On the Title page

Item [73] Assignee: please add --Shionogi & Co., Ltd., Osaka, Japan--.

Signed and Sealed this

Twenty-third Day of February, 1993

Attest:

STEPHEN G. KUNIN

*Attesting Officer*   Acting Commissioner of Patents and Trademarks